(12) United States Patent
Young et al.

(10) Patent No.: US 7,069,929 B2
(45) Date of Patent: Jul. 4, 2006

(54) DRY POWDER INHALER

(75) Inventors: Matthew Young, Hertfordshire (GB);
Stuart Kay, Hertfordshire (GB); Neil
Harrison, Hertfordshire (GB); James
Welsh, Tyne and Wear (GB); Michael
Ligotke, San Diego, CA (US)

(73) Assignee: Quadrant Technologies Limited (GB)

( * ) Notice: Subject to any disclaimer, the term of this
patent is extended or adjusted under 35
U.S.C. 154(b) by 501 days.

(21) Appl. No.: 10/099,592

(22) Filed: Mar. 15, 2002

(65) Prior Publication Data

US 2002/0170560 A1 Nov. 21, 2002

Related U.S. Application Data

(63) Continuation-in-part of application No. 09/773,261,
filed on Jan. 31, 2001, now Pat. No. 6,715,486, which
is a continuation-in-part of application No. 09/495,
494, filed on Feb. 1, 2000, now Pat. No. 6,427,688.

(51) Int. Cl.
*A61M 15/00* (2006.01)
*B65D 83/06* (2006.01)

(52) U.S. Cl. ................. 128/203.15; 128/203.21;
128/203.12; 604/58

(58) Field of Classification Search ........... 128/203.15,
128/203.21, 203.12; 604/58
See application file for complete search history.

(56) References Cited

U.S. PATENT DOCUMENTS

| 4,841,964 | A |   | 6/1989  | Hurka et al. |           |
|-----------|---|---|---------|--------------|-----------|
| 5,388,572 | A |   | 2/1995  | Mulhauser et al. |       |
| 5,921,237 | A |   | 7/1999  | Eisele et al. |          |
| 6,116,238 | A | * | 9/2000  | Jackson et al. | 128/203.15 |
| 6,484,715 | B1 | * | 11/2002 | Ritsche et al. | 128/200.21 |
| 6,792,945 | B1 | * | 9/2004  | Davies et al. | 128/203.15 |

* cited by examiner

*Primary Examiner*—Henry Bennett
*Assistant Examiner*—Andrea M. Ragonese
(74) *Attorney, Agent, or Firm*—Perkins Coie LLP

(57) ABSTRACT

A dry powder inhaler includes an actuator pivotably
mounted on a base. Movement of the actuator from a first
position to a second position drives the a dobber to open a
blister. A dispersion engine sub-assembly has a blister hood
positioned over a blister opening position. A powder path-
way connects from the blister hood into a powder dispersion
engine. Upon inhalation, air flow draws powder up and out
of an opened blister, into the blister hood and to the powder
dispersion engine. Movement of the actuator causes the
dobber to shear open a blister and also to press the blister
hood down over the blister. This increases air flows up and
around the open blister, carrying the pharmaceutical powder
up and out of the blister and into the dispersion engine.

20 Claims, 18 Drawing Sheets

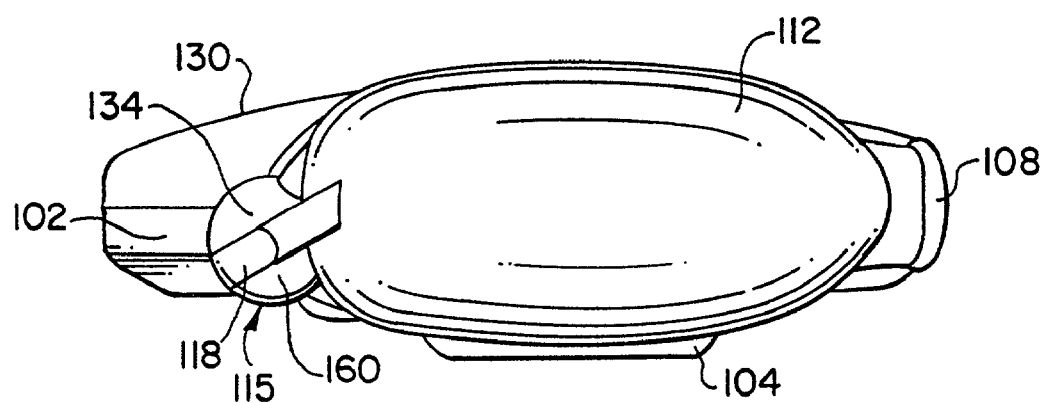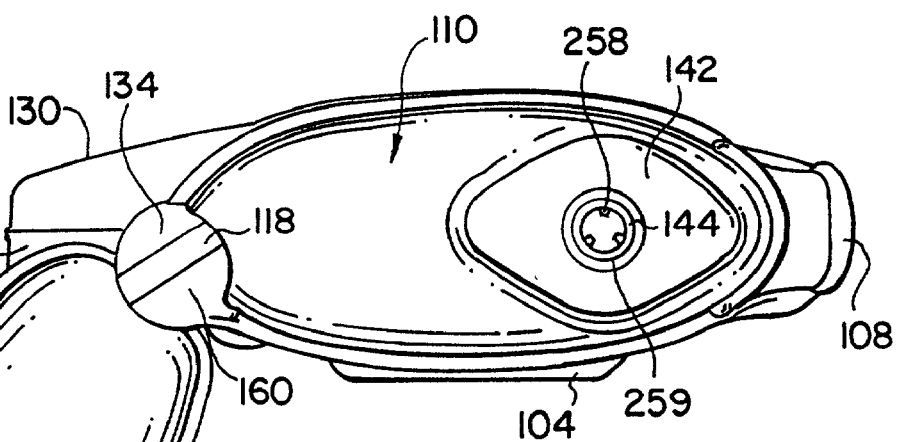

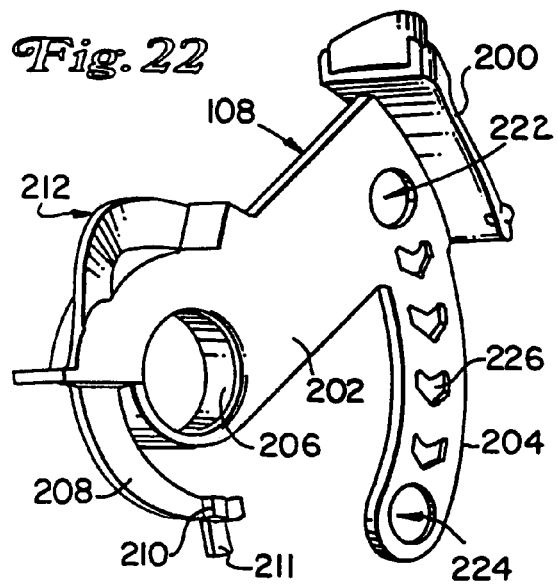
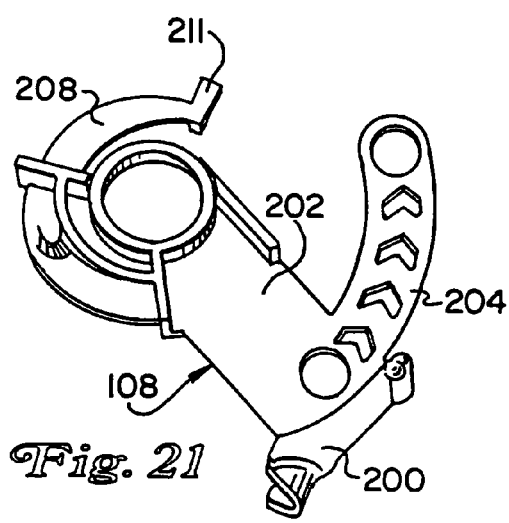
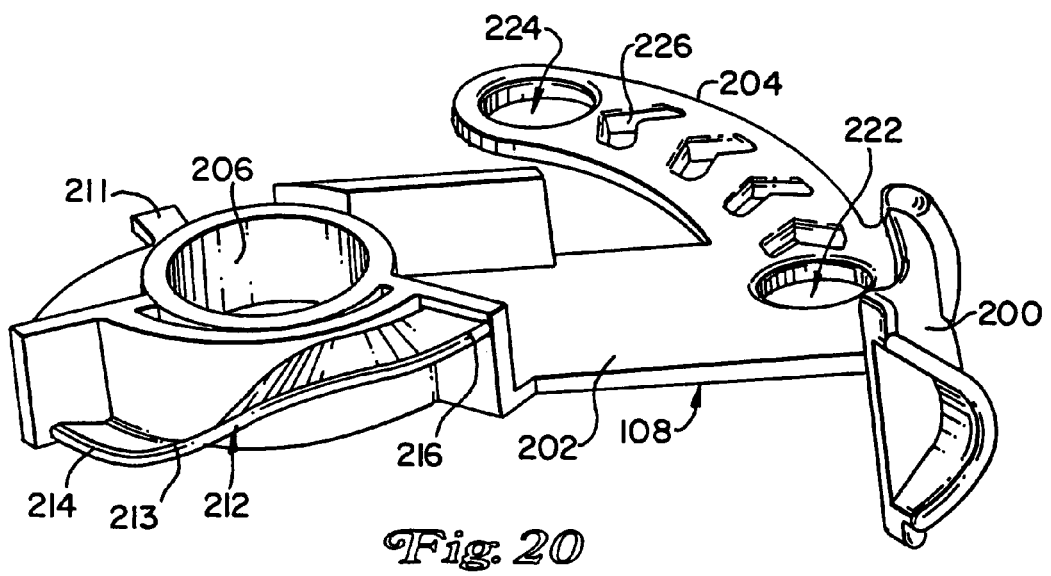

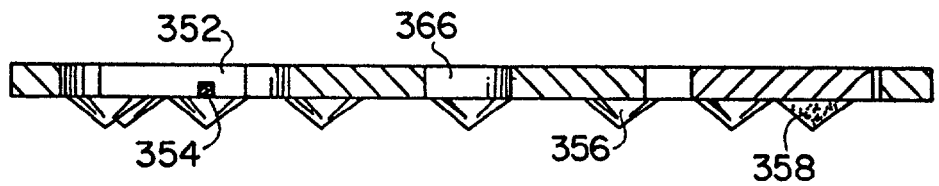
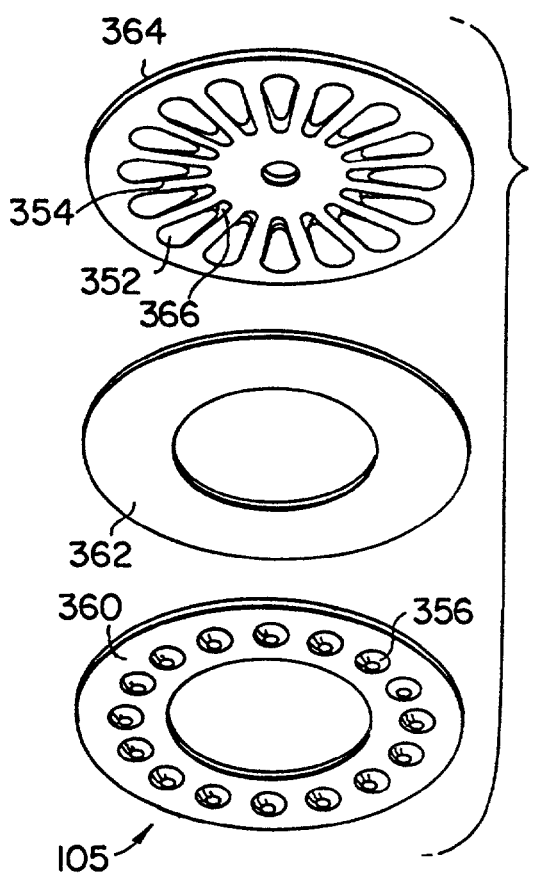
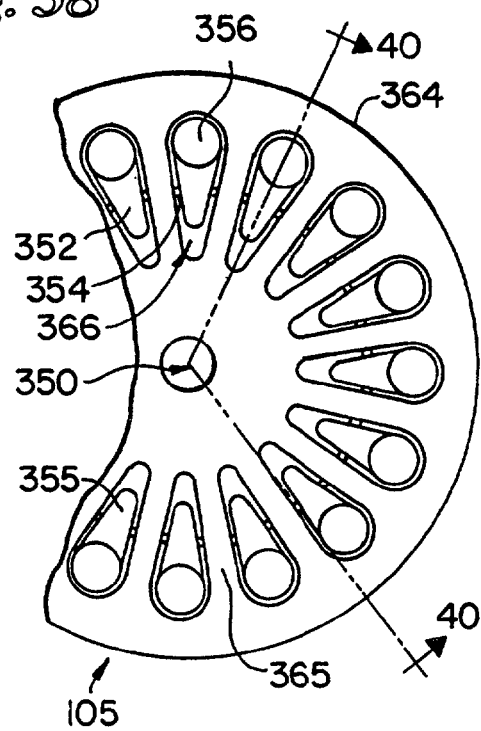

DRY POWDER INHALER

This application is a Continuation-in-Part of U.S. patent application Ser. No. 09/773,261, filed Jan. 31, 2001 now U.S. Pat. No. 6,715,486, which is a Continuation-in-Part of U.S. patent application Ser. No. 09/495,494, filed Feb. 1, 2000 now U.S. Pat. No. 6,427,688. Priority to these applications is claimed under 35 U.S.C. § 120 and these Applications are incorporated herein by reference.

The field of the invention is inhalers.

BACKGROUND OF THE INVENTION

Inhalers are used to deliver drugs into a patient's lungs. Typically, an inhaler contains or provides a mixture of drug particles and air or propellant gas. The mixture is delivered via the patient inhaling from a mouthpiece on the inhaler with the air or propellant gas carrying the drug particles into the patient's lungs.

In dry powder inhalers, the drug particles, in the form of a fine dry powder, are entrained into an airflow, and inhaled by the patient, for treatment for various conditions, for example, bronchial asthma. Drugs delivered via a dry powder inhaler can be used to treat many conditions, including those unrelated to lung conditions, via the systemic absorption of the drug into the bloodstream, via the lung.

For effective dose delivery using a dry powder inhaler, the powder particles must first be dispersed to form a powder/air aerosol. Various techniques for forming powder aerosols have been proposed. Some of these techniques use the airflow from the patient's inspiration alone to disperse the powder. Other techniques involve forming a powder aerosol by spinning a propeller within a chamber; generating a fast moving flow of air over or through the powder; and shaking, vibrating, or impacting a powder laden string, tape, or mesh, using mechanical devices or ultrasonics. In addition, various other techniques for generating powder aerosols have been proposed or used, with varying degrees of success. Challenges remain in achieving a dry powder inhaler which can effectively create a dry powder aerosol for inhalation, while also having advantages in other areas, such as effectiveness in creating an aerosol, reliability, complexity of design, costs, ergonomics, dose consistency, and other factors.

Dry powder inhalers have certain advantages over metered dose inhalers and nebulizers or liquid droplet inhalers. Typically, dry powder inhalers do not require propellant gases, which may be damaging to the environment. Dry powder inhalers generally also do not require a high level of user coordination between releasing a dose and inhaling the dose. As they do not release a burst or high speed plume of drug particles, having the release of the dose occur near simultaneously with inhalation is not required. Dry powder inhalers can also have relatively reliable and inexpensive designs.

Various techniques have been proposed for storing doses of powder in a dry powder inhaler. These techniques include bulk storage of the powder in a reservoir having a metering out device, gelatin capsules which are pierced or cut open, or blister disks having individual blisters which are punctured or sheared open. To better seal the pharmaceutical powder from the environment (to reduce caking, contamination, or other undesirable changes), individually sealed dose containers such as blister disks, are preferred. Inhalers using blister disks have had different ways of advancing the blister disk to deliver sequential doses, of opening the blisters, and of moving the powder out of the open blister for inhalation by the user. While test results on some of these types of inhalers have been promising, engineering challenges remain in providing reliable and accurate blister disk operations in a dry powder inhaler, while also providing advantageous human factors features.

Accordingly, it is an object of the invention to provide an improved dry powder inhaler.

SUMMARY OF THE INVENTION

Concepts of the invention include: pivotal movement of an actuator used for opening a blister; an actuator that moves into a position blocking movement of a retainer, to prevent installation of a blister disk unless the actuator is at or near its home position; use of a blister disk with the blister facing up, so that air flow draws powder up and out of the blister; an anti-double dose system using an up-facing blister, where the powder remains in the open blister, and is not moved into a dispersion or other chamber, until inhalation by the user; a blister hood which can be displaced into contact with a blister disk during inhalation, and spaced apart from the blister disk to allow the blister disk to advance one position.

In a first aspect, an inhaler for providing multiple doses of a pharmaceutical powder from blisters on a blister disk includes an actuator pivotably mounted on a base. The actuator preferably includes a ramp. A dobber or plunger is engaged with the ramp on the actuator. Movement of the actuator from a first position to a second position causes the ramp to drive the dobber to open a blister.

In a second aspect, the base includes a tray retainer moveable between opened and closed positions, and with the actuator moveable to a position at least partially overlying the tray retainer, when the tray retainer is in the closed position.

In a third aspect, the tray retainer is moveable from a closed position, wherein it secures a blister disk tray assembly onto a first side of the base. The tray retainer is also moveable to an open position, where it is spaced apart from the base, to allow removal and replacement of the blister disk tray assembly.

In a fourth aspect, an inhaler includes a blister hood positioned over a blister opening position. A powder pathway connects from the blister hood into a powder dispersion engine in the inhaler. Upon inhalation, air flow draws powder up and out of an opened blister, into the blister hood and to the powder dispersion engine.

In a fifth aspect, the powder dispersion engine includes an engine tube having to inwardly projecting ribs acting as an air flow restriction.

In a sixth aspect, the dobber is positioned so that movement of the actuator causes the dobber to shear open a blister on a blister disk, and also to press the blister hood down over, or into contact with blister disk. Upon inhalation, an increased amount of air flows up and around the open blister, carrying the pharmaceutical powder up and out of the blister and into the dispersion engine.

In a seventh and separate aspect, a dust cap is attached to the inhaler housing with a hinge oriented at an acute angle to the housing.

In a method for operating a dry powder inhaler, a tray holding a blister disk is installed into the inhaler. An actuator is pivoted in a first direction to open a blister on the blister disk. Upon inhalation, the pharmaceutical powder is conducted up and out of the open blister and into a dispersion engine, via inhalation air flow. The powder is dispersed in air in the dispersion engine. The actuator is pivoted back in the reverse direction, to advance the blister disk in the tray.

A blister disk tray assembly for use with a dry powder inhaler includes a blister disk pivotably supported on a mounting hub. A lock out ratchet is spring biased into engagement with the blister disk, preventing any pivotal movement of the blister disk. When used in an inhaler, returning movement of an actuator in the inhaler momentarily disengages the lock out ratchet from the blister disk, allowing the actuator to incrementally advance the blister disk by one position, to bring a subsequent blister into position for opening.

Other and further aspects and advantages will appear in the following detailed description taken in connection with accompanying drawings. While a single embodiment is shown and described, the drawings and description are intended to provide an overview of the general concepts of the inventions. Various alternative designs and equivalents may of course be used.

The invention also contemplates sub-combinations of the various components, subassemblies and method steps described. The various aspects described above need not all necessarily be included in the invention. Rather they can generally be used independently, or in various combinations and sub-combinations.

BRIEF DESCRIPTION OF THE DRAWINGS

In the drawings, wherein the same element number represents the same element, throughout the several views:

FIG. 4 is a front view of the inhaler of FIG. 1, with the dust cap shown in the closed position.

FIG. 5 is a front view of the inhaler of FIG. 1, with the dust cap shown in an open position.

FIG. 20 is a top and left perspective view of the actuator shown in FIG. 13.

FIG. 21 is a top view of the actuator of FIG. 20.

FIG. 22 is a top and left side perspective view of the actuator of FIG. 20.

FIG. 38 is an exploded perspective view of the blister disk shown in FIGS. 31 and 32.

FIG. 39 is a top view of the blister disk shown in FIG. 38.

FIG. 40 is a section view taken along line 40—40 of FIG. 39.

DETAILED DESCRIPTION

Figure 1:
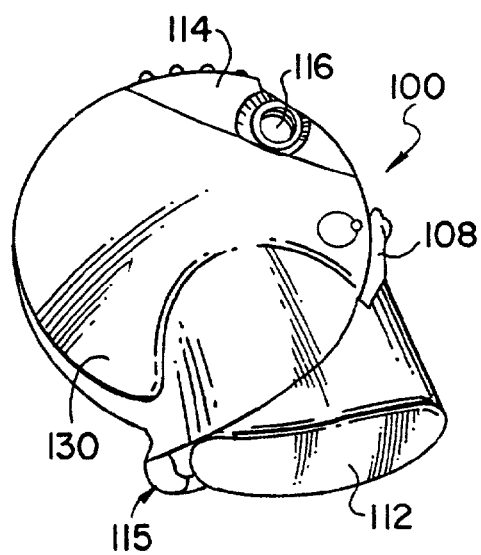
FIG. 1 is a top perspective view of a novel dry powder inhaler, shown in the stored position.
Figure 2:
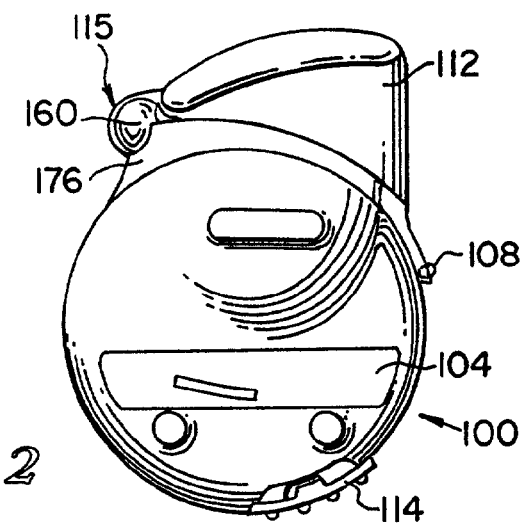
FIG. 2 is a bottom view of the inhaler of FIG. 1.
Figure 3:
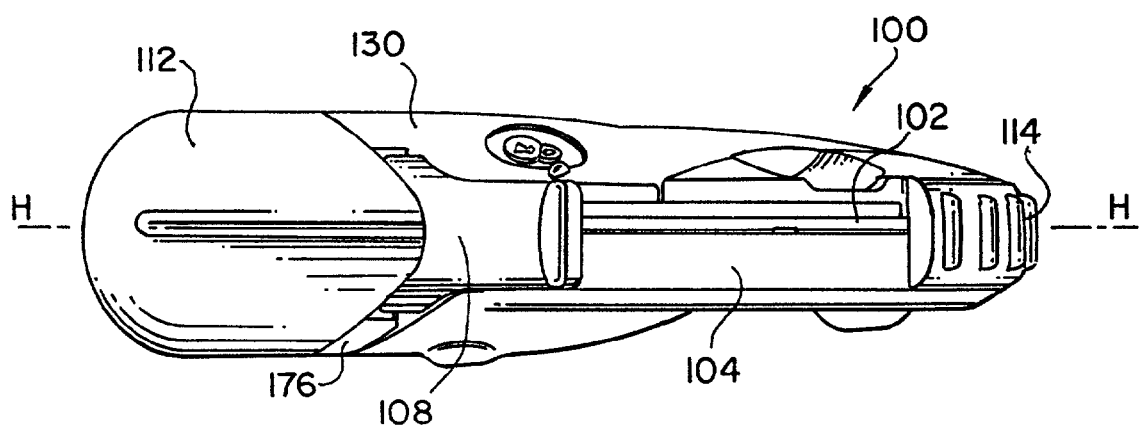
FIG. 3 is a right side view of the inhaler of FIG. 1.
Figure 6:
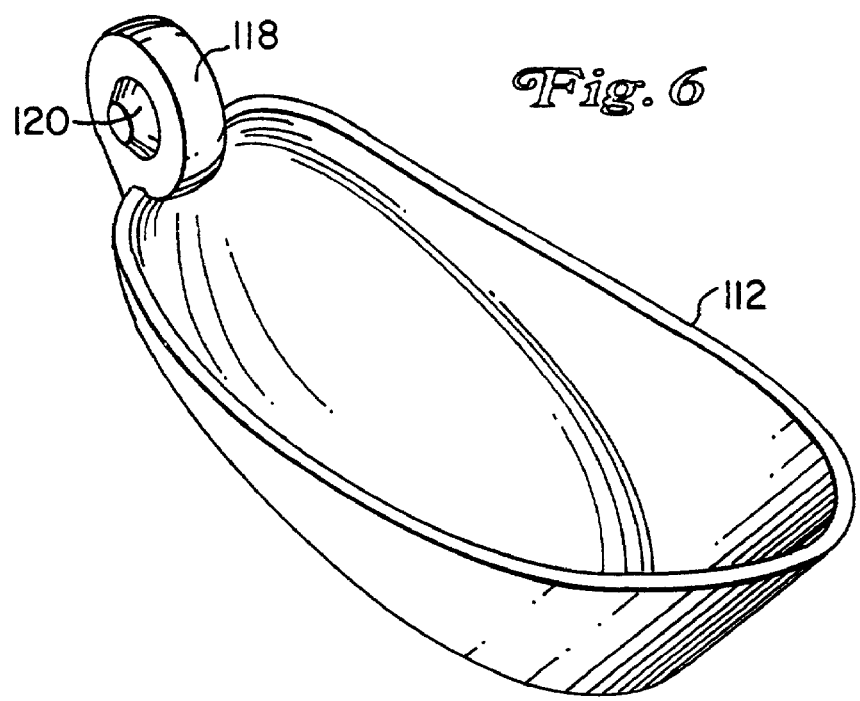
FIG. 6 is a top perspective view of the dust cap shown in FIGS. 4 and 5.
Figure 7:
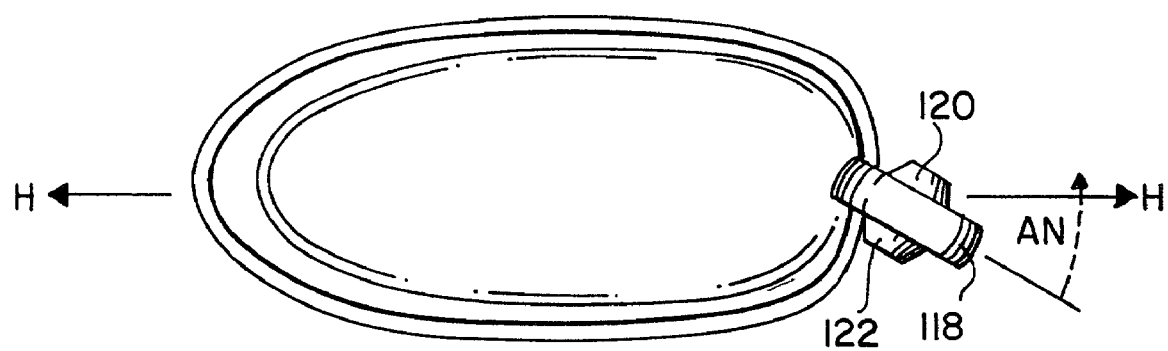
FIG. 7 is a rear view of the dust cap shown in FIG. 6.

Turning now in detail to the drawings, as shown in FIGS. 1–4, an inhaler 100 has a mouthpiece frame 176 on a base or base plate 102. A dust cap 112 is pivotably secured to the base plate 102 via an angled hinge 115. A blister disk tray assembly 104 is attached or engaged to the bottom surface of the base plate 102. A tray retainer 114 secures the tray assembly 104 in place on the base plate 102. An actuator 108 is pivotably moveable over a sector of about 50–80 or 60–70 degrees to actuate the inhaler 100. A top cover 130 is attached over the top surface of the base plate 102.

Figure 11:
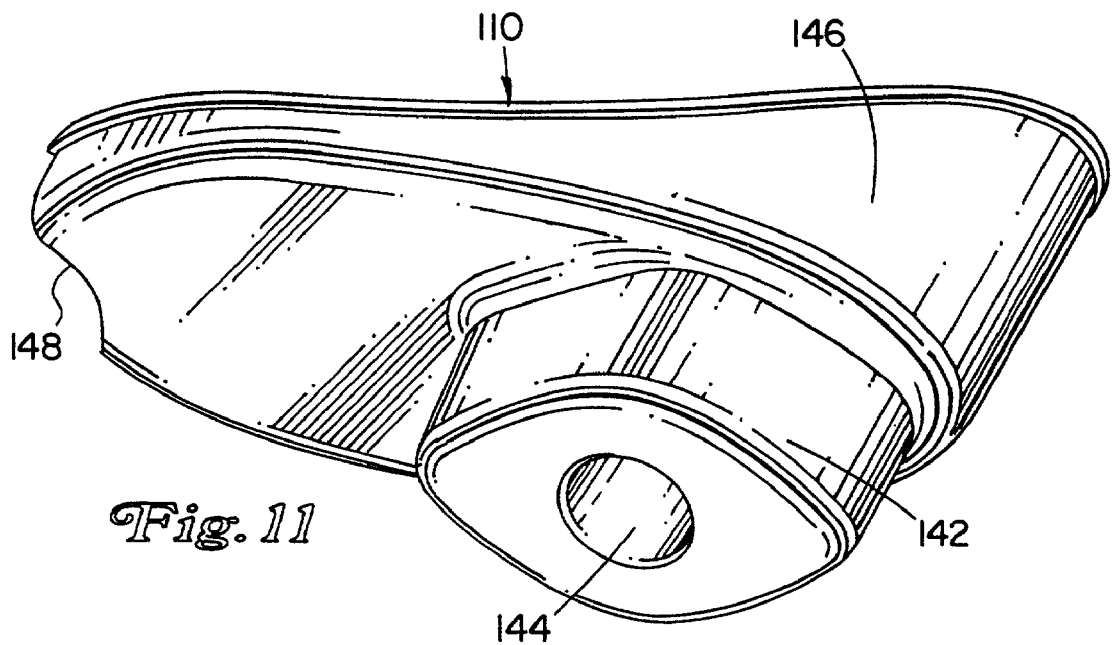
FIG. 11 is a front perspective view of the mouth piece on the inhaler shown in FIG. 5.
Figure 12:
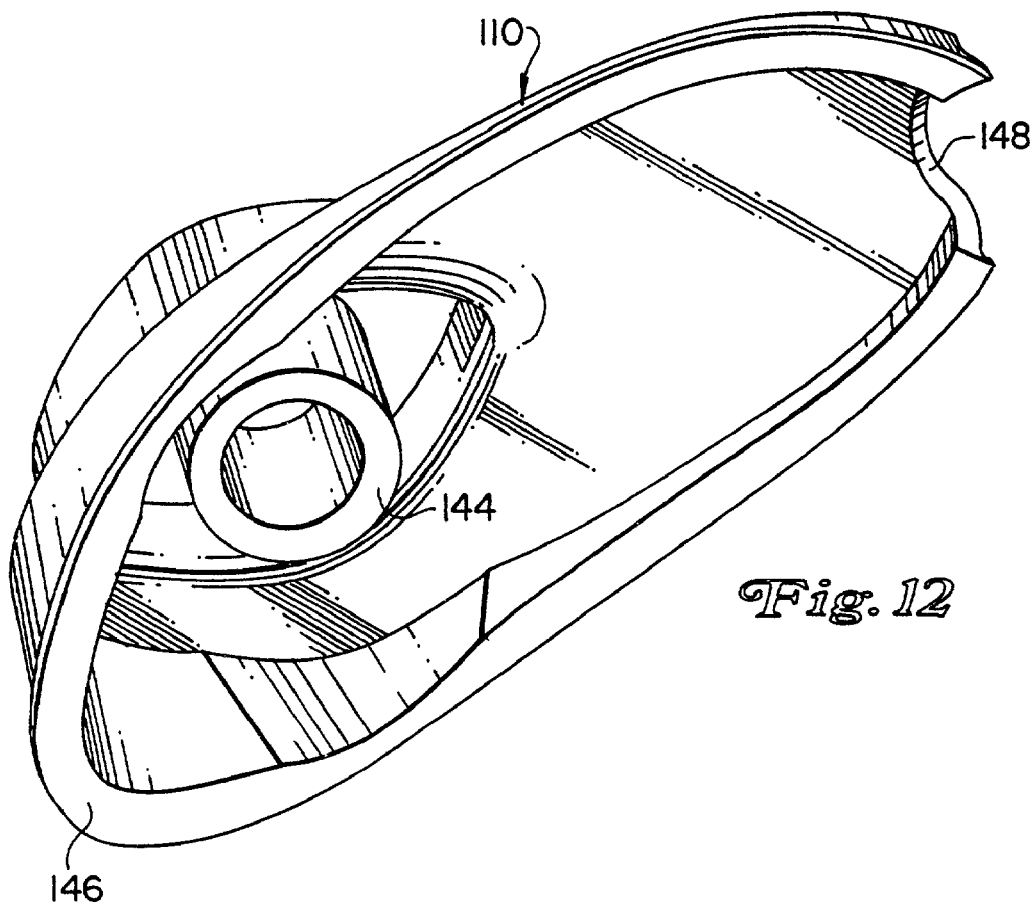
FIG. 12 is a rear perspective view of the mouth piece of FIG. 11.

As shown in FIGS. 4–7, the hinge assembly 115 includes a hinge plate 118 on the dust cap 112 secured between a hinge top 134 on the top cover 130 and a hinge bottom 160 on the base plate 102. The hinge plate 118 is oriented at an acute angle AN of 15–45°, 20–40°, 25–35° or 30° relative to the dust cap horizontal axis H—H. The axis H—H is parallel to the plane (the flat top or bottom surfaces) of the base plate 102. In use, the inhaler 100 is held with axis H—H horizontal or near horizontal (perpendicular to gravity). Axles 118 and 120 on the hinge plate extend into and are pivotably secured by the hinge bottom 160 and hinge top 134. A mouthpiece 110, shown in FIGS. 11 and 12, is attached to the mouthpiece frame 176 on the base plate 102. As shown in FIG. 5, when the dust cap 112 is pivoted to the open position, the dust cap moves both down and away from the mouthpiece 110. This provides added clearance around the mouthpiece. Hence, the dust cap does not interfere with use of the inhaler.

Figure 8:
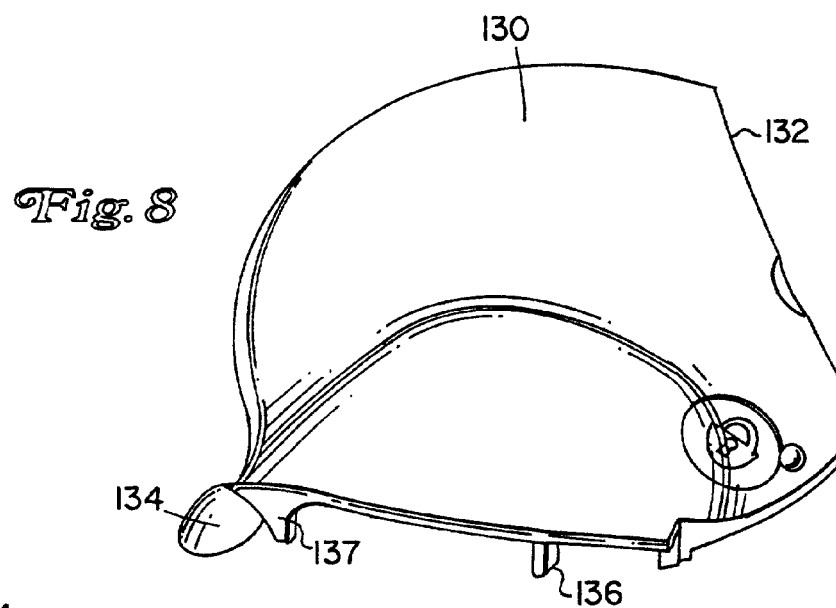
FIG. 8 is a top perspective view of the top cover of the inhaler shown in FIG. 1.
Figure 9:
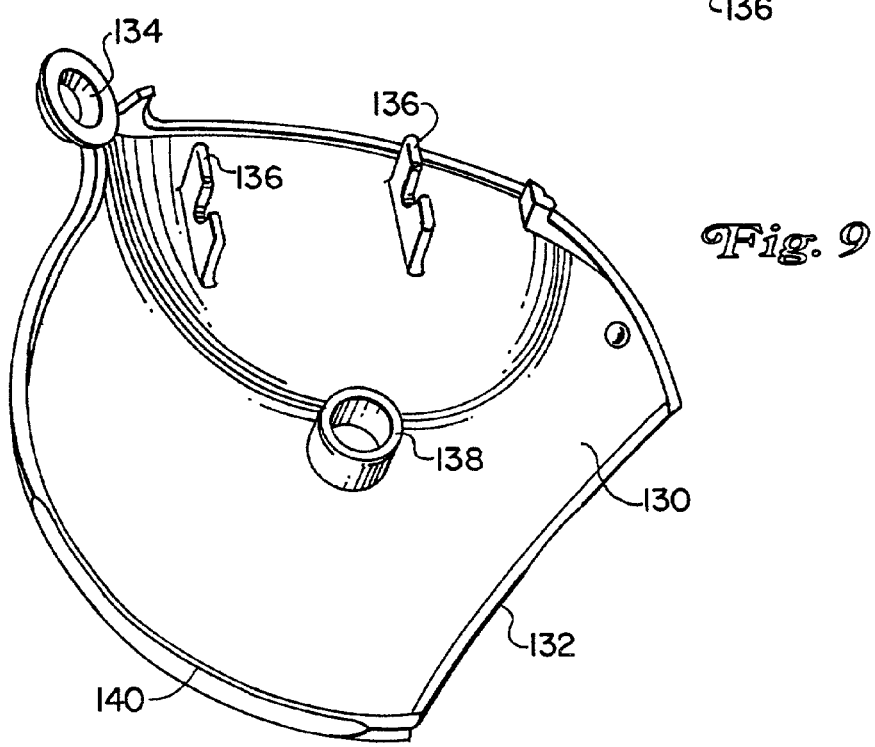
FIG. 9 is a bottom perspective view of the cover shown in FIG. 8.
Figure 10:
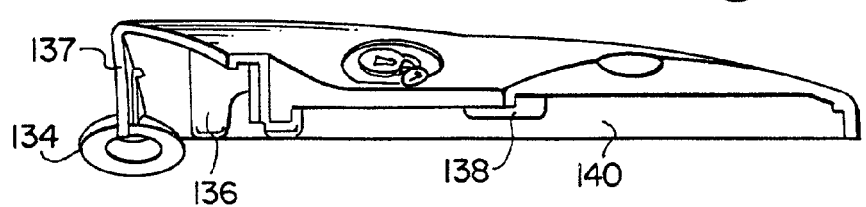
FIG. 10 is a right side view of the cover shown in FIGS. 8 and 9.

Turning to FIGS. 8–10, the top cover 130 has upper dobber supports 136 near the front and generally opposite to a back edge 132. A cover hub 138 is generally centrally located on the bottom surface of the cover 130. The hinge top 134 is attached to a front wall 137 of the cover 130, generally at an angle AN to the plane of the cover.

Turning to FIGS. 11 and 12, the mouthpiece 110 has a stem 142 on a rear cup or base 146. A mouthpiece tube 144 extends through the stem 142. A notch 148 at the left end of the cup 146 provides clearance for the hinge assembly 115, when the inhaler components are assembled. The stem 142 is smoothly contoured. In use, the users lips may be comfortably placed around the stem. Referring momentarily to FIG. 5, the stem 142 is offset to the right side of the inhaler. This provides additional clearance between the stem 142 and the dust cap 112, when the inhaler is in use.

Figure 13:
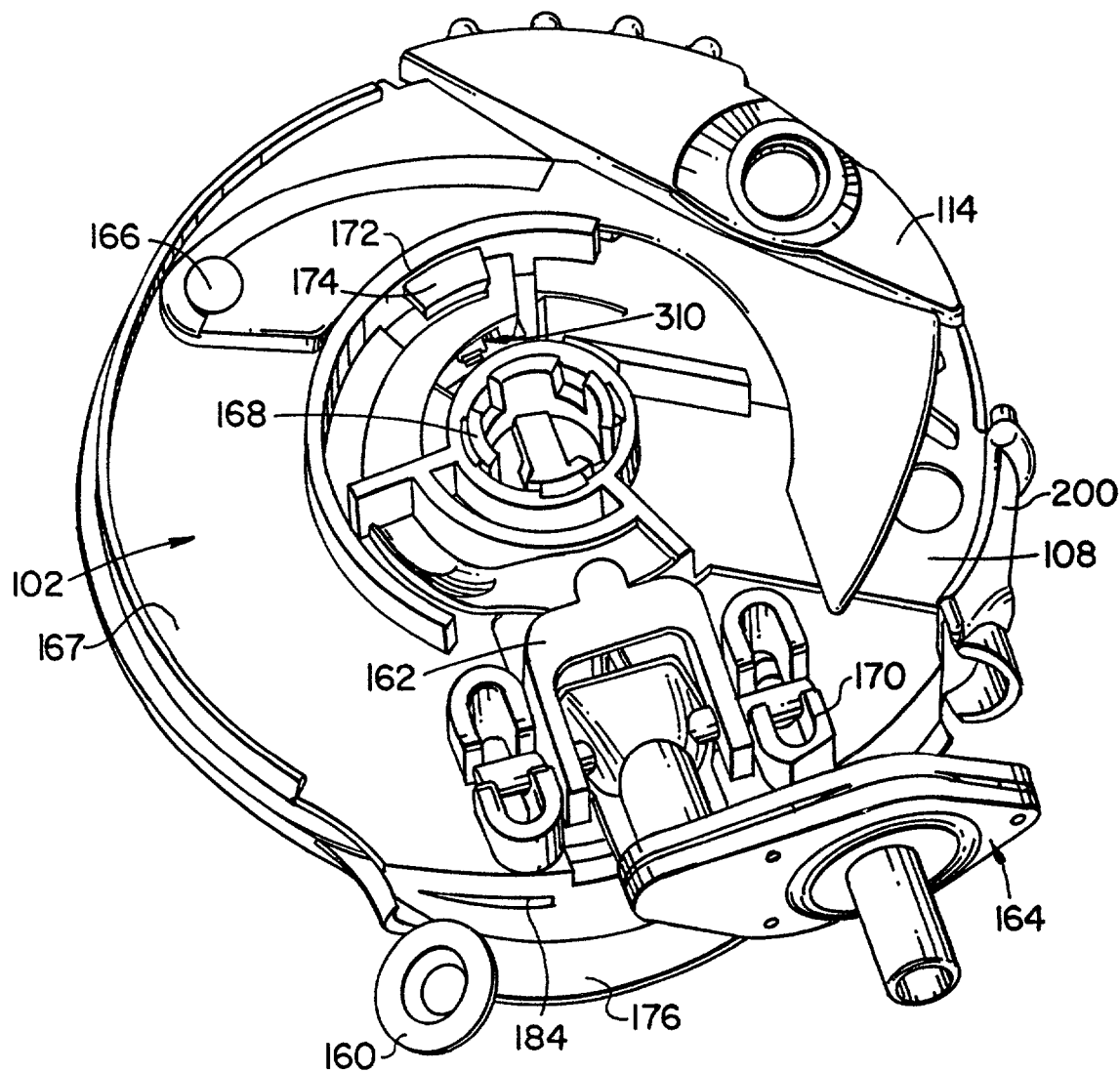
FIG. 13 is a top and front perspective view of the inhaler shown in FIG. 1, with the top cover shown in FIG. 8 removed.

Turning now to FIG. 13, which shows internal components of the inhaler 100, the actuator 108 is pivotably attached to a central hub 168 on the top surface 167 of the base plate 102. A powder dispersion engine 164 is attached to the front of the base plate 102. The tray retainer 114 is pivotably attached to a pin 166 on the top surface of the base plate 102. A dobber 162 is pivotably supported on the base plate 102 adjacent to the dispersion engine 164. As described in detail below, in use, the actuator drives the dobber to open a blister on a blister disk in the blister disk tray assembly 104.

Figure 14:
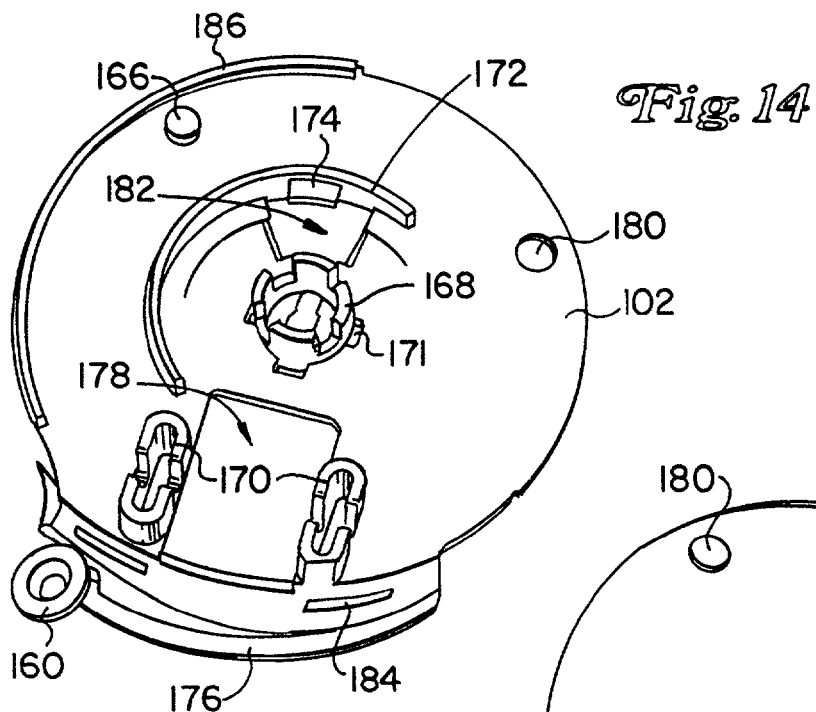
FIG. 14 is a top and front perspective view of the base plate shown in FIG. 13.
Figure 15:
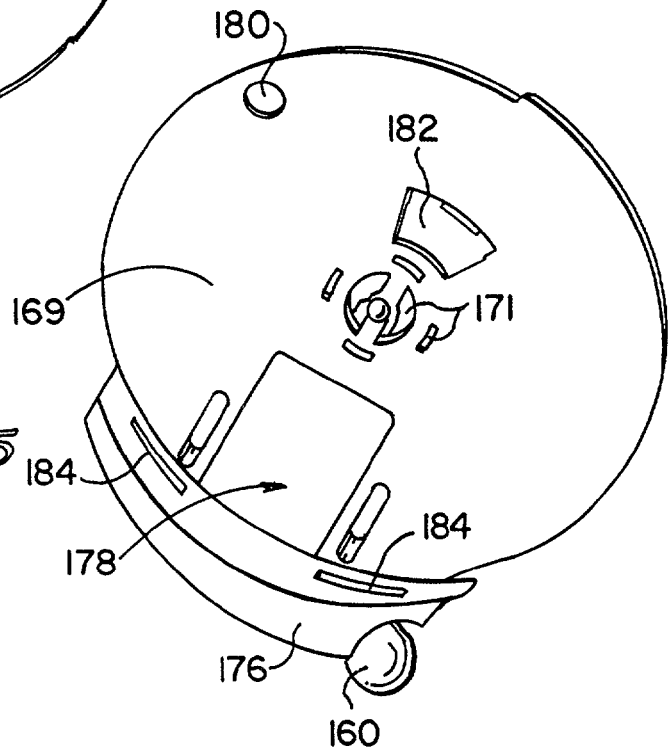
FIG. 15 is a bottom and rear perspective view of the base plate of FIG. 14.
Figure 16:
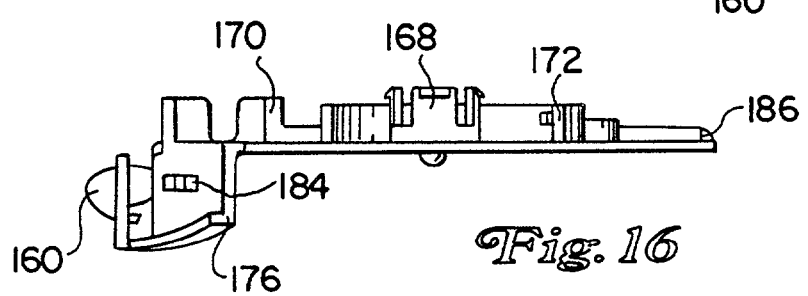
FIG. 16 is a right side view of the base plate shown in FIG. 14.

The base plate 102 is shown in detail in FIGS. 14–16. The mouthpiece frame 176 is attached to and extends down from the bottom surface 169 of the generally circular base plate 102. A dobber opening 178 extends through the base plate 102 between the mouthpiece frame 176 and the hub 168, which is generally centered on the base plate 102. Openings 171 are provided around the hub 168 to better facilitate manufacture. A dose indicator base plate window 180 extends through the base plate 162. A ramp 172 on the top surface of the base plate 102 cooperates with the actuator 108, as described below.

Figure 17:
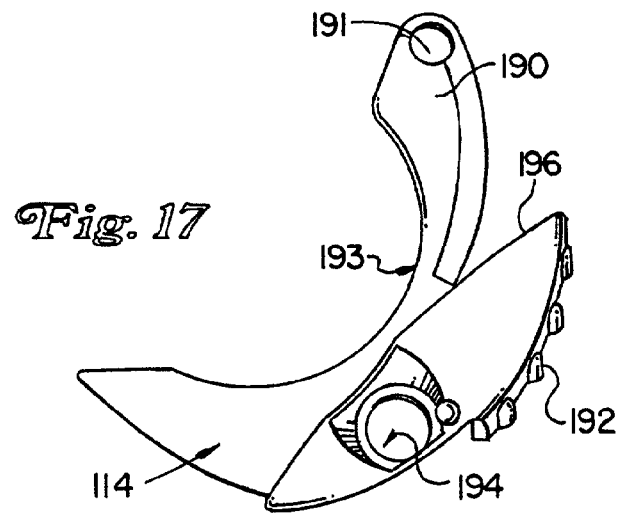
FIG. 17 is a top view of the blister disk tray latch shown in FIGS. 1, 3 and 13.
Figure 18:
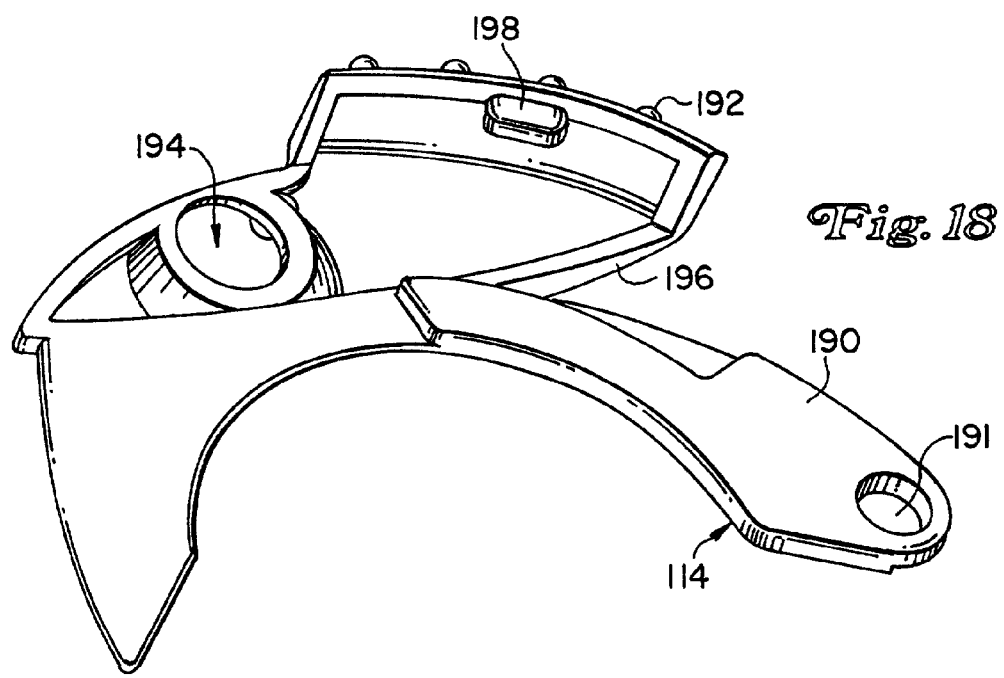
FIG. 18 is a top perspective view of the latch of FIG. 17.
Figure 19:
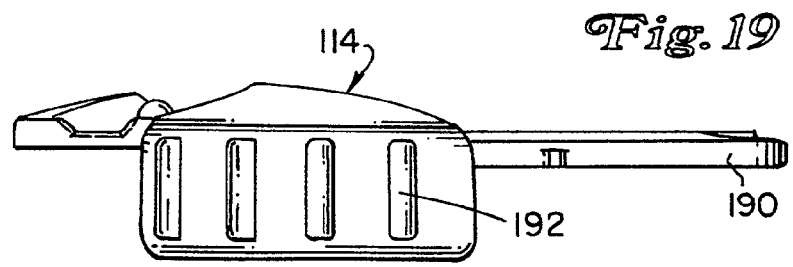
FIG. 19 is a right side view of the latch of FIG. 17.
Figure 23:
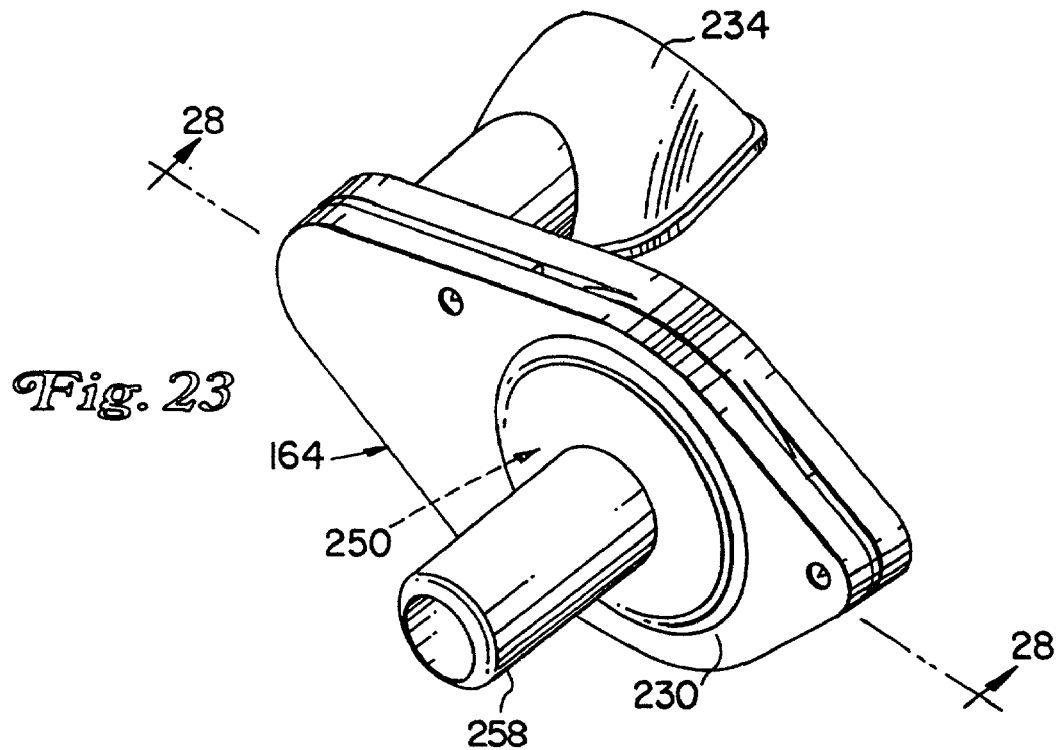
FIG. 23 is a top perspective view of the dispersion engine shown in FIG. 13.
Figure 24:
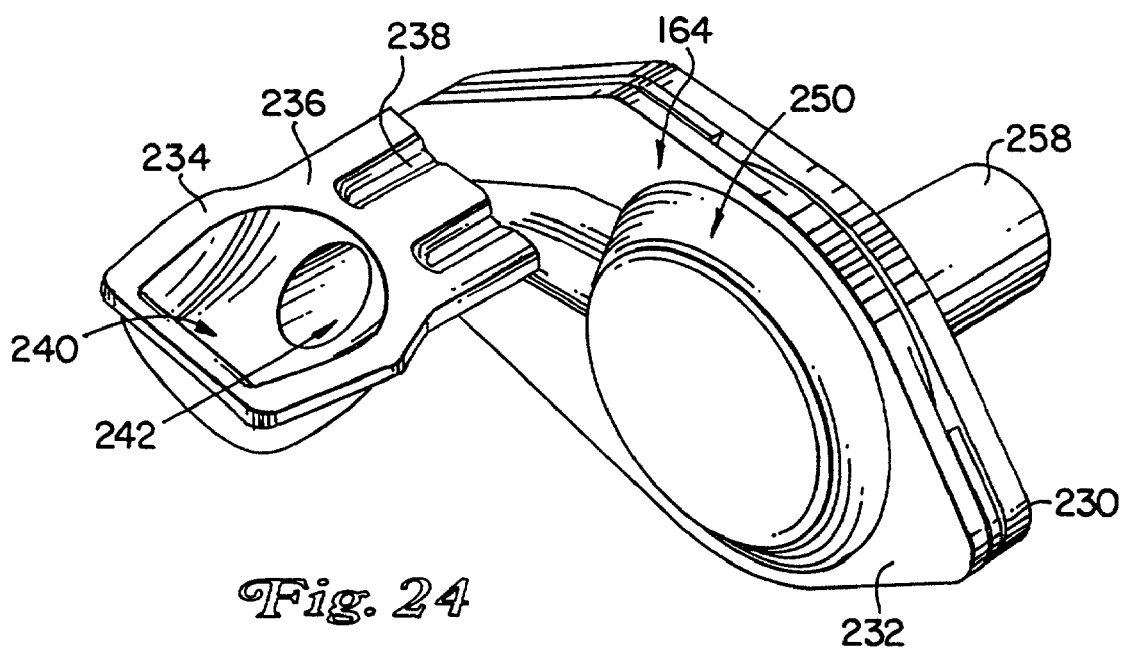
FIG. 24 is a bottom perspective view of the dispersion engine shown in FIG. 23.

As shown in FIGS. 17–19, the tray retainer 114 has an opening 191 at the end of a pivot arm 190 which is pivotably attached onto the pin 166 on the base plate 102. A finger grip 192 on the pivot arm 190 has a window 194 and an inward facing tray tooth 198. The inner edge 196 of the finger grip 192 is contoured to match the back edge 132 of the cover 130, as shown in FIG. 1. The curved inside surface 193 of the pivot arm 190 generally conforms to the radius of the ramp 172 on the base plate 102. The retainer 114 may be replaced with various equivalents such as latches, snaps, gates and similar devices. The term "retainer" in the claims means a component or feature that helps to hold the blister disk (or other drug carrier) onto the inhaler.

Referring to FIGS. 20–22, the actuator 108 has a curved finger plate 200 attached to an arm 202 connecting to a hub opening 206. A ramp flange 212 extends partially around the hub 206. An advancing finger 208 is attached to the ramp flange. A blister disk engaging tooth 210 on the advancing finger 208 advances a blister disk in the tray assembly 104 with movement of the actuator. A movement indicator 204 attached to the arm 202 has first and second windows 222 and 224, and arrows 226 which help provide visual operating instructions to the user. The ramp flange 212 has a center section 213 having a compound curvature, bounded by a flat start section 214 and a flat end section 216. The center section curves both vertically and horizontally, like an involute screw thread, to better engage with the dobber 162 over the range of movement of the actuator 108. The actuator may have various forms. The term "actuator" in the claims means a component or feature that the user moves, directly or indirectly, to open a blister (or other drug container).

Figure 30:
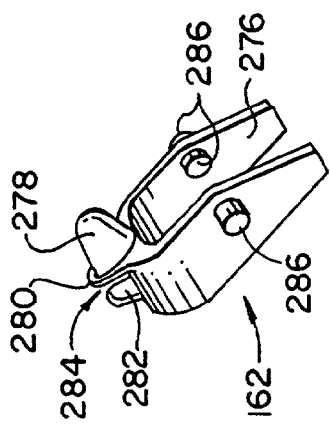
FIG. 30 is a bottom perspective view of the dobber shown in FIG. 13.

Referring momentarily to FIG. 30, the dobber 162 has first and second legs formed in a U-frame 276. Axle stubs 286 extend outwardly on each of the legs of the U-frame. A cam tooth 278 extends downwardly from a tooth plate 280 on the U-frame. An actuator plate 282 is spaced apart from the tooth plate 280. The ramp flange 212 of the actuator 108 fits into the slot 284 formed between the tooth plate 280 and the actuator plate 282, when the components are assembled. The term "dobber" means a component or feature moved directly or indirectly by an actuator, for opening a blister or other drug container.

Pivotal movement of the actuator 108 consequently drives the dobber to pivot about the axle stubs 286, to shear open a blister on the blister disk. The dobber supports 136 on the underside of the top cover engage the axle stubs, and hold them in place from above, along with the supports 170 on the base plate 102, which engage and hold the axle stubs from below.

Turning now to FIGS. 24–27, an engine back 232 has a back bead race 246 formed within a chamber back plate 235. Attachment pins 244 extend forward from the back plate 235. A blister hood 234 is formed on a hood plate 236 attached generally perpendicularly to the back plate 235. A hood chamber 240 is formed within the blister hood. A hood duct 242 extends through the blister hood and connects with an inlet 248 on the front surface of the engine back 232. A back inlet recess 249 extends from the inlet 248 to the back race 246. Grooves 238 may be provided in the hood plate 236 to adjust its bending characteristics.

Figure 27:
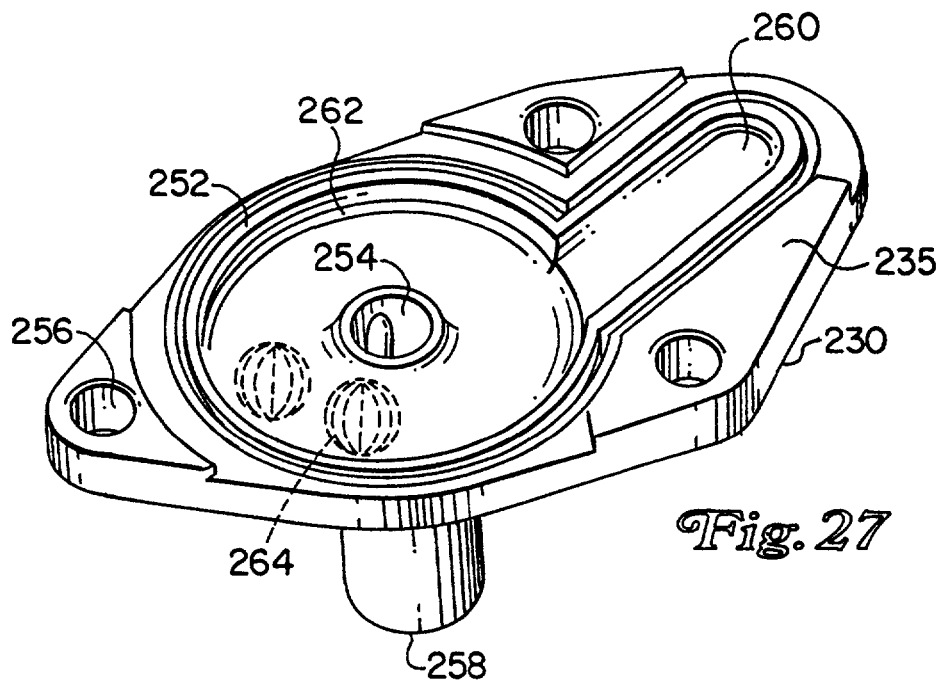
FIG. 27 is a rear perspective view of the engine front shown in FIG. 23.
Figure 26:
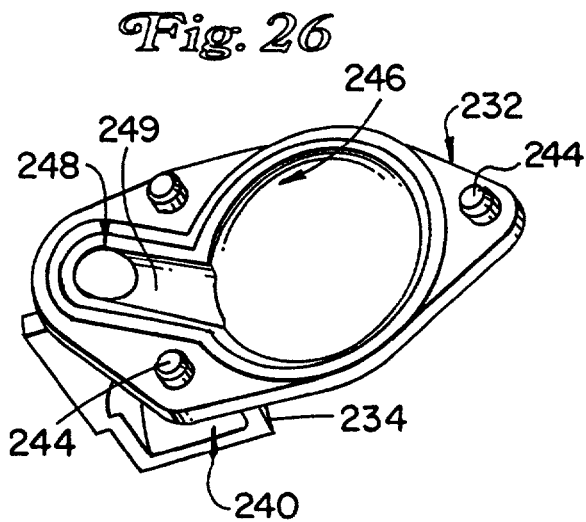
FIG. 26 is a front perspective view of the engine back of FIG. 25.
Figure 25:
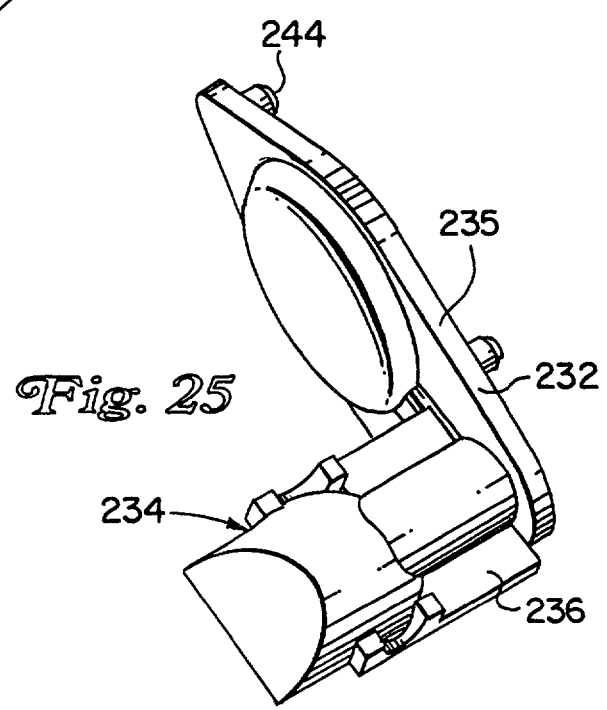
FIG. 25 is a top and rear perspective view of the dispersion engine back.

Referring to FIG. 27, an engine front plate 230 has a front bead race 262 surrounding a chamber outlet 254, and matching the size and shape of the back bead race 246 in the engine back 232. The chamber outlet 254 connects into an engine tube 258 extending forward from the engine front 230. Pin openings 256 are positioned and adapted to mate with the attachment pins 244 on the engine back 232. A front inlet recess 260 in the back surface of the engine front plate connects in the back bead race 246 and is formed as a mirror image of the inlet recess 249 in the engine back 232.

Referring now to 23, 24, and 27–29, the powder dispersion engine 164 is formed by the combination of the engine back 232 and the engine front 230. The attachment pins 244 pass through the pin openings 256 to secure the engine back and engine front together. The back race 246 aligns with the front race 262 and forms a bead chamber 250. Beads 264 are provided in the bead chamber 250, before assembly, as described in International Patent Application PCT/US01/03248, incorporated herein by reference. The term "beads" means one or more objects which can move freely within the dispersion chamber to disperse powder. While the above-described dispersion engine 164 is preferred, other dispersion techniques may also be used, including for example, engines without beads or any moving parts, engines having fixed or moving, powered or free spinning vanes or propellers, engines using compressed gases, electrostatic vibratory, piezo electric, or other techniques.

Figure 28:
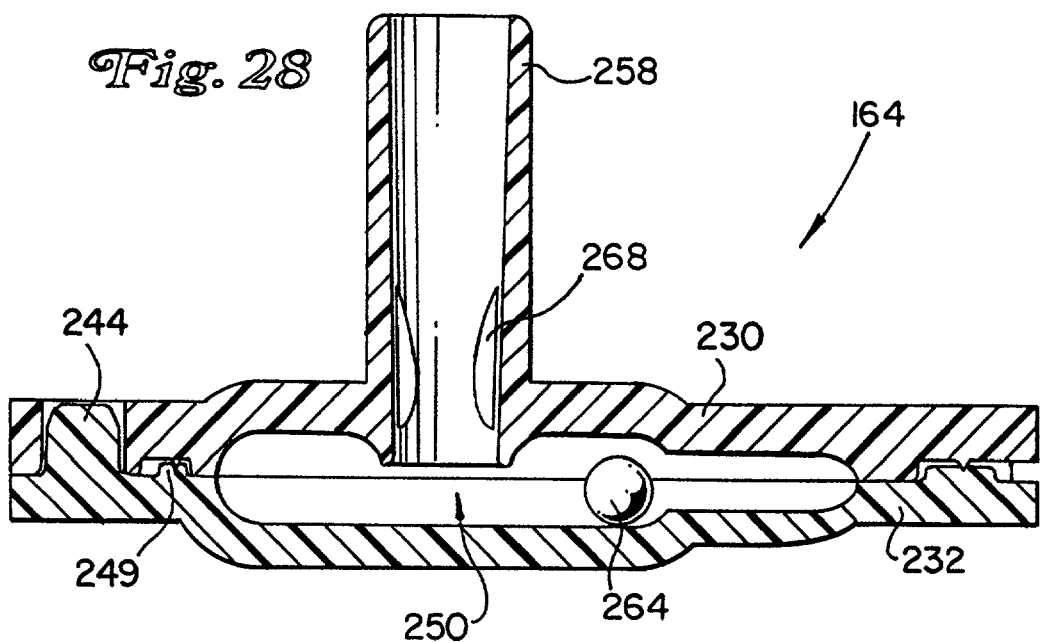
FIG. 28 is a section view of the dispersion engine shown in FIG. 23, and taken along line 28—28 of FIG. 23.
Figure 29:
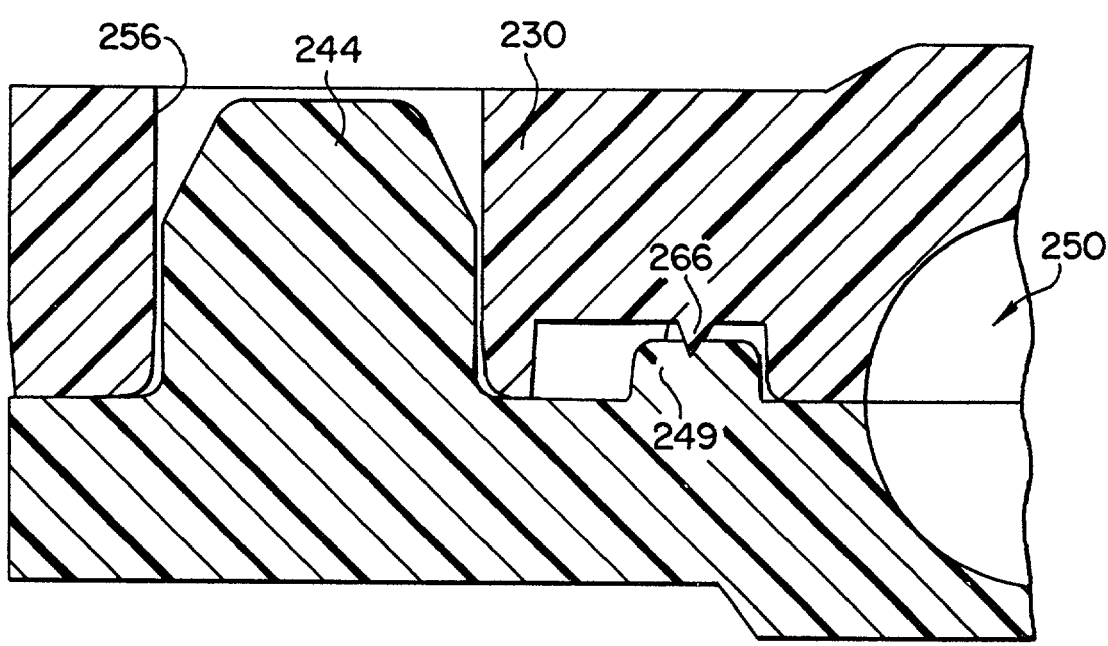
FIG. 29 is an enlarged detail of the left side of FIG. 28.

Referring to FIGS. 28 and 29, when the engine back 232 is attached to the engine front 230, a lip ring 266 on the engine front engages into a raised area 249 on the engine back, to better close off or seal the bead chamber 250 (except at the inlet and engine tube 258). As shown in FIG. 28, ribs 268 extend radially into the engine tube 258. The ribs form a restriction in the tube, which accelerates flow during inhalation. As shown in FIG. 5, when assembled, the engine tube 258 extends concentrically through the tube 144 in the mouthpiece 110.

Turning now to FIGS. 31 and 33–35, the tray assembly 104 is made up of a tray 290 and a blister disk 106. The tray has a front wall 295 adapted to engage with the back side of the mouthpiece frame 176. Tabs 314 on the front wall 295 extend into corresponding slots 184 on the back surface of the mouthpiece frame 176, as shown in FIG. 37.

Referring to FIG. 34, the blister disk 106 is pivotably attached to a post 300 located generally at the center of the generally round tray 290. The post 300 preferably has locking spring arms 301 or other permanent fastener, to prevent separation of the blister disk 106 from the tray 290. A ratchet lock 310 extends upwardly and engages a spoke 365 of the blister disk 106, to prevent pivoting or turning movement of the blister disk 106, in either direction (clockwise or counter clockwise), when the tray assembly 104 is separated from the inhaler 100. The ratchet lock 310 is momentarily depressed by the actuator to allow for incremental advancing movement of the blister disk 104.

A blister tab base wall 308 extends around the tray 290, except at the blister opening position 309. The base wall 308 helps to maintain the tabs of the blister disk 106 in a flat or planar position as the disk 106 incrementally pivots within the tray during use, especially after the tabs are actuated to release a dose of powder. A first outer wall 304 supports the perimeter of the blister disk 106.

Figure 37:
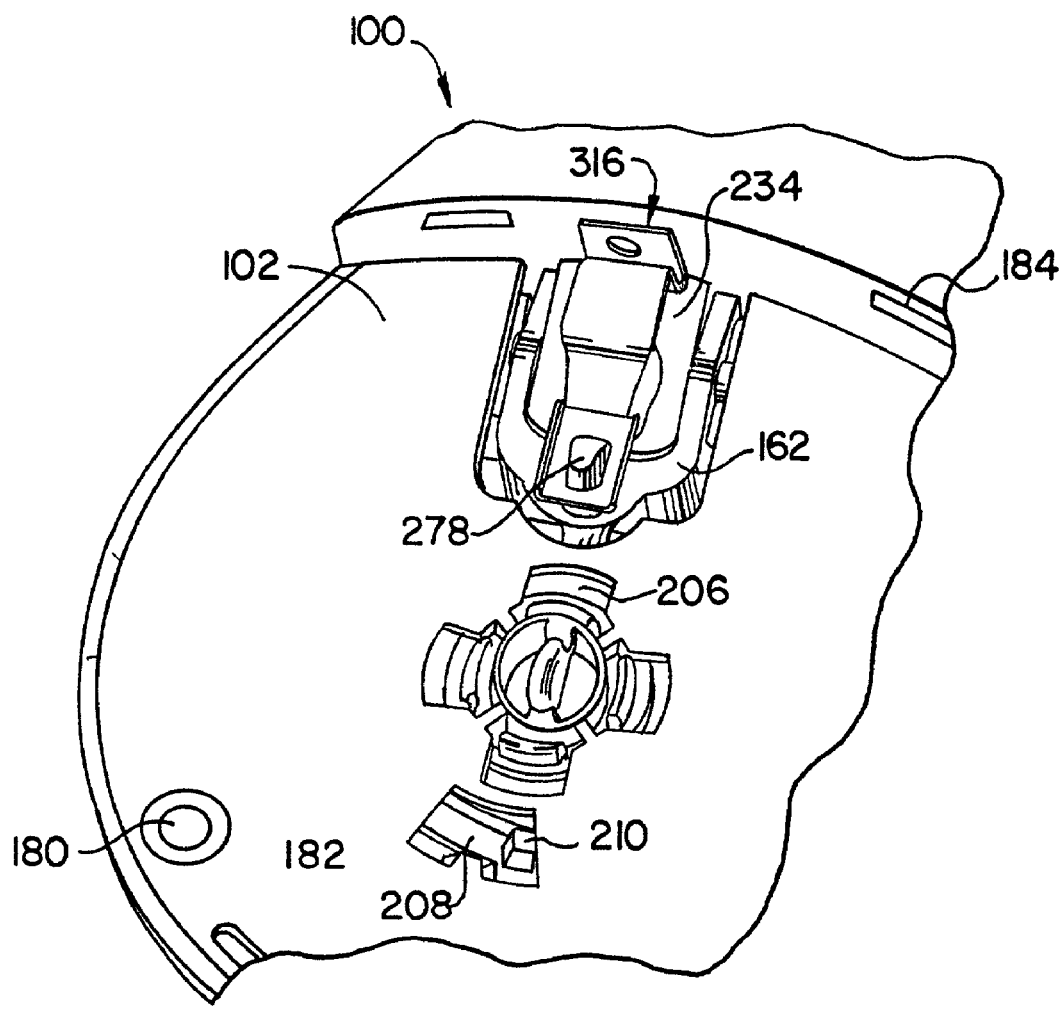
FIG. 37 is a partial top perspective view of the inhaler of FIG. 1, with the blister disk tray assembly removed and with the tray spring of FIG. 36 shown in position, for clarity of illustration.
Figure 36:
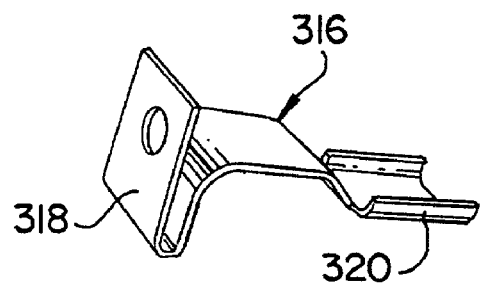
FIG. 36 is a bottom and side perspective view of the blister disk tray spring shown in FIG. 31.

As shown in FIGS. 36 and 37, a return spring 316 has a clip section 318 which attaches to the front wall 295 of the tray 290, with an arm section 320 of the spring extending into the blister opening position 309. The arm section 320 of the return spring 316 acts to return the tabs of the blister disk 106 to their starting position, after the tab is actuated to release a dose of powder from a blister.

Figure 33:
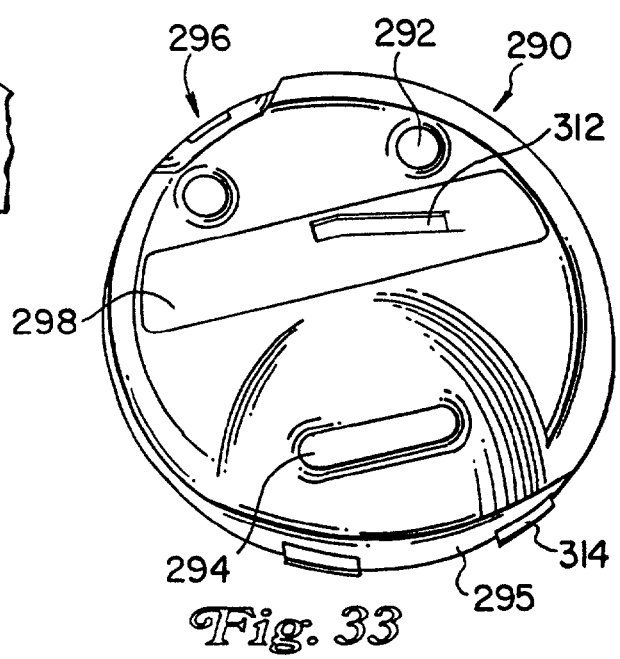
FIG. 33 is a bottom view of the blister disk tray shown in FIG. 31.

As shown in FIG. 33, the bottom surface of the tray 290 has feet 292 and 294, to allow the tray 290 to rest on a flat surface without tipping or rocking. An opening 312 under the ratchet lock, facilitates manufacturing by injection molding. A label recess 298 is provided around the opening 312.

Figure 31:
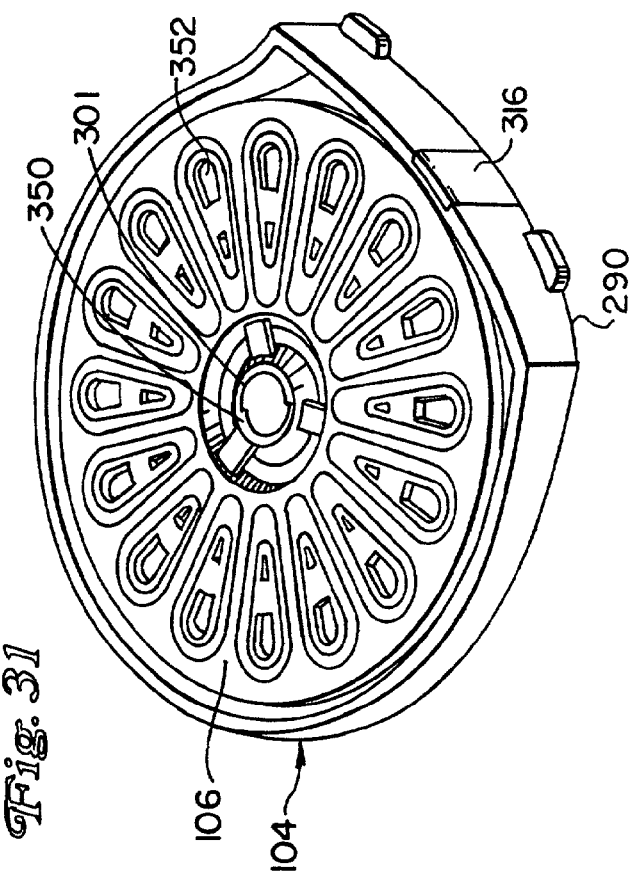
FIG. 31 is a top perspective view of the blister disk tray assembly shown in FIG. 2.
Figure 32:
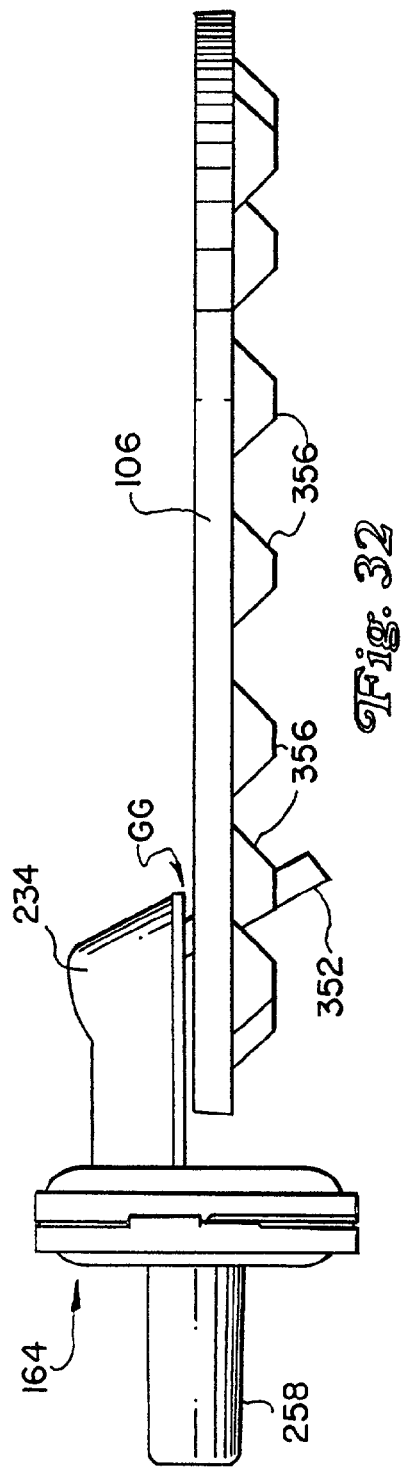
FIG. 32 is a side view of the dispersion engine of FIG. 23 and the blister disk of the blister disk tray assembly shown in FIG. 31.
Figure 34B:
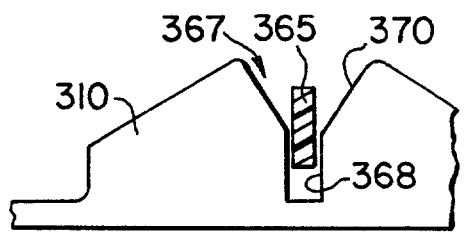
FIG. 34B is an enlarged front view of the ratchet lock shown in FIG. 34A.

Turning now to FIGS. 31 and 38–40, the blister disk 106 preferably includes a hard plastic base disk 364, and a metal foil shear layer 362 and a blister layer 360. Blisters 356 containing a pharmaceutical powder 358 are formed in the blister layer 360. The shear layer 362 is adhered to the blister layer 360 and to the disk 364. The disk 106 includes a plurality of tabs 352 equally radially spaced apart and supported on pivot arms 354. Each of the tabs 352 can pivot within a cutout 366 in the base disk 364, by an amount sufficient to open the shear layer 362 and release the powder 358 in the blister 356. Tab openings 366 around each of the tabs 352 are separated by spokes 365. The bottom surface of each spoke is formed with an acute angle or a radius, to allow for more secure engagement of each spoke by the rachet lock 310 on the tray 290. A center mounting hole 350 in the base disk 364 fits over the post 300 on the tray 290. The details of the blister disk 106 are described in International Patent Publication WO 96/33759 incorporated herein by reference. In use, in the inhaler 100, the bottom or blister side of the disk is facing down, while the tab side of the blister disk, shown in FIG. 39 face up towards the base plate 102. As shown in FIG. 32, the blisters open "up," i.e., the shear layer forms the top of the sealed blister compartments.

Figure 41:
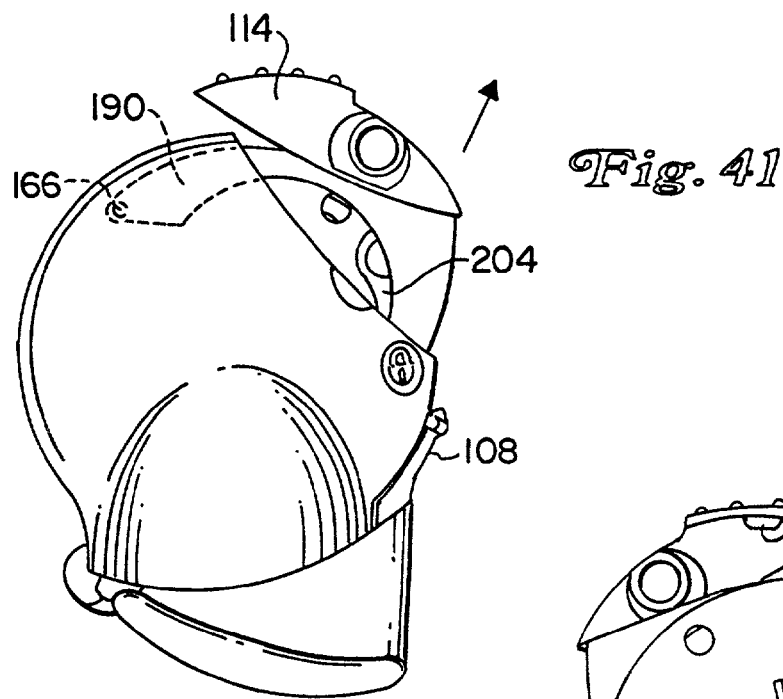
FIG. 41 is a top view of the inhaler of FIG. 1 with the blister disk tray latch in the open position.
Figure 42:
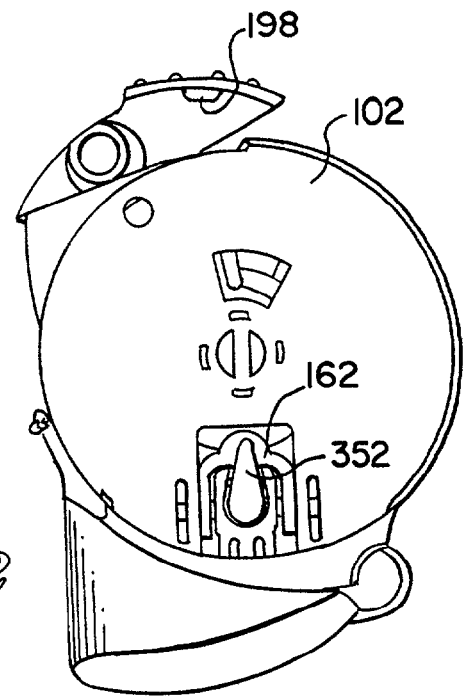
FIG. 42 is a bottom view of the inhaler as shown in FIG. 41, with the blister disk tray assembly of FIG. 31 removed.
Figure 43:
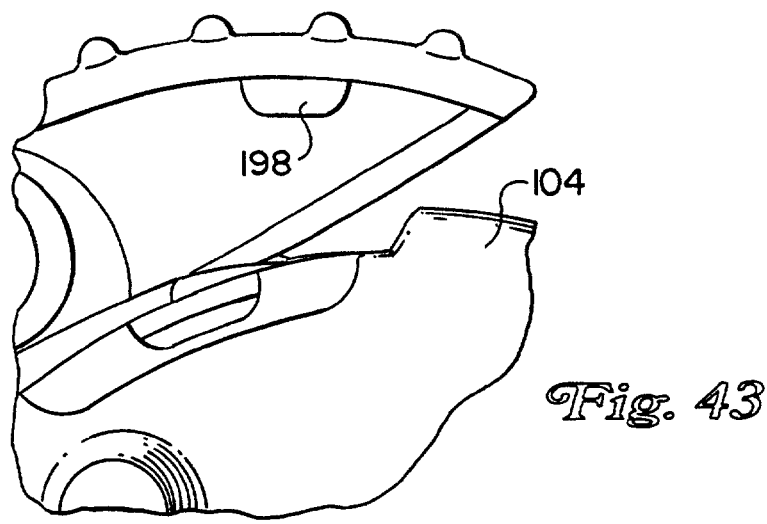
FIG. 43 is an enlarged detail of the latch shown in FIG. 42.

Operation of the inhaler is now described. To install or replace the tray assembly 104, the tray retainer 114 is pivoted outwardly about the retainer pivot post 166. Referring to FIGS. 41–43, the actuator 108 is in the home or stored position. The tray assembly 104, as shown in FIG. 31, is removed from its packaging and is installed onto the inhaler 100. Specifically, the front wall 295 of the tray 290 is positioned against the back wall of the mouthpiece frame 176. Referring momentarily to FIGS. 15, 34 and 37, the guide tabs 314 extending forwardly from the front wall 295 of the tray 290 are inserted into the tab slots 184 on the back wall of the mouthpiece frame 176. The tray 290 is then moved into contact with, and sits substantially flush against the base plate 102. The tray retainer 114 is then pivoted inwardly, to secure the tray assembly 104 in place. The retainer tooth 198 shown in FIG. 18 snaps into the indent 296 at the back of the tray 290, to secure the tray assembly 104 in place. The inhaler 100 then appears as shown in FIG. 1, i.e., with a tray assembly 104 installed, and with the tray retainer 114 and actuator 108 in the home positions. The tabs 314 and slots 184 can be keyed so that only tray assemblies 104 having a specified pharmaceutical, can be installed onto the inhaler.

Referring to FIGS. 13, 34A, 34B and 39, when the tray assembly 104 is separated from the inhaler 100, the lockout ratchet 310 is constantly in an up position engaged around one of the spokes 365 of the blister disk 106, preventing any pivotal movement of the blister disk 106. This prevents inadvertent advancing of the blister disk within the tray (in either direction) which could result in loss of the ability to access doses in skipped blisters, or actuation of a blister which was previously accessed, resulting in no dose delivered. Even with the tray assembly 104 attached to the inhaler, the lockout ratchet 310 remains constantly engaged on one of the spokes 365, to prevent pivotal movement of the blister disk 106, except at the moment when the actuator is returned to the home position, as described below. The ratchet lock has a y-shaped slot 367 having a lower section with straight sidewalls 368 and an upper section with angled sidewalls 370. When engaged, a spoke 365 of the blister disk is positioned at least part way between the straight sidewalls.

Figure 44:
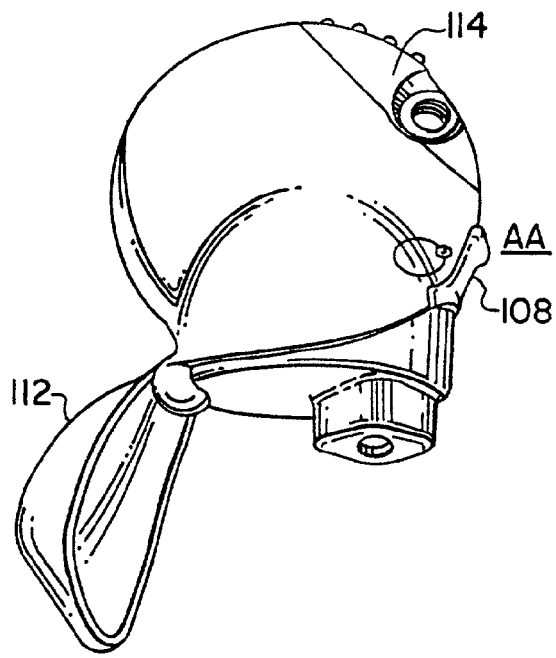
FIG. 44 is a top and front perspective view of the inhaler of FIG. 1, with the dust cap open and the actuator in the home or stored position.
Figure 45:
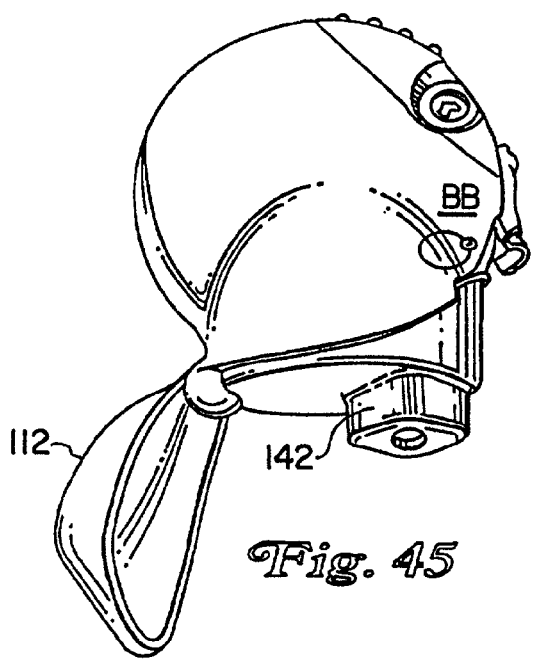
FIG. 45 is a top and front perspective view of the inhaler of FIG. 44 with the actuator moving towards an inhale position.
Figure 46:
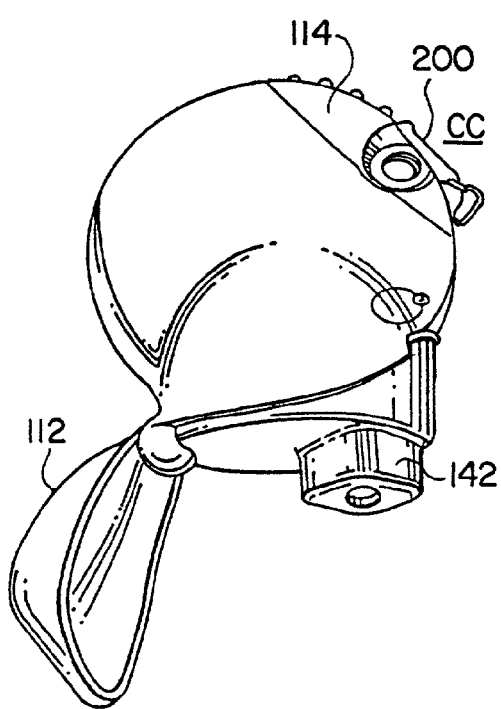
FIG. 46 is a top and front perspective view of the inhaler of FIG. 44, with the actuator moved fully into the inhale position.

Referring to FIGS. 44–46, the user pivots the dust cap 112 open. To open a blister and deliver a dose of powder, with the inhaler near horizontal, the user pushes or slides the actuator 108 from the stored position AA in FIG. 44, to the inhale position CC shown in FIG. 46. This causes the finger plate 200 of the actuator 108 to move over the tray retainer 114.

Referring to FIGS. 13 and 44–46, as the finger plate 200 is pushed from the home or stored position AA to the inhale position CC, the actuator 108 pivots circumferentially about the central hub 168. The advancing tooth 210 and finger 208 ride up and over the guide 174. The ramp flange 212 of the actuator pivots the dobber 162 about the axle stubs 286. The cam tooth 278 on the dobber 162 presses down on the inner section 355 of the tab 352 located at the blister opening position 309. The blister tab 352 pivots on the pivot arms 354, shearing open the blister 356. The dose is then ready to be inhaled.

The patient places the stem 142 of the mouthpiece 110 into the mouth and inhales. Air is drawn through the inhaler 100, over the now open blister 356 into the hood chamber 240, through the inlet 242 and into the bead chamber 250 of the dispersion engine 164. The blister hood 234 is positioned directly over the (opened) blister at the blister opening position 309.

As the dobber 162 moves down to pivot the blister tab 352 to open a blister, the arm 320 of the return spring 316 is pushed down by the bottom surface of the blister tab 352. The dobber 162 also presses the blister hood 234 down slightly, as the dobber reaches the limit of pivoting movement. This causes the blister hood 234 to flex downwardly and contact the blister disk. The space or gap GG between the blister hood 234 and the disk 106, shown in FIG. 32, is closed. Consequently air flow into the blister hood is confined to space over the open blister. As a result, powder from the blister is more efficiently lifted out and entrained in the air stream. When the actuator is reversed, the dobber lifts up and the blister hood separates from the blister disk, allowing the blister disk to advance. The hood plate 236 has sufficient flexibility to allow for this movement of the hood (typically about 0.1–0.3 mm).

The end sections 214 and 216 of the ramp flange 226 are flat, so as to not create any further travel of the dobber 120 near the limits of travel. This allows the actuator 108 to change direction more easily.

The geometry of the interaction between the dobber 162 and the blister tab 352 on the blister disk 106 is set up so that during initial contact, the cam tooth 278 on the dobber contacts the inside tip of the tab. This provides added leverage for shearing open the blister. As the blister tab 352 begins to pivot, the cam tooth 278 moves inwardly, closer to the pivot arms 354, providing increased pivoting movement of the tab relative to the movement of the dobber. With this design, and the design of the ramp flange, the interaction between the dobber and the blister tab provides increased leverage and force at the beginning of movement, to shear open the blister, followed by decreased force, but increased travel, after shearing of the shear layer 362 has commenced.

As the user inhales on the mouthpiece, air flows over and around the opened blister 356. The powder in the blister 356 is entrained into the air flow. The air/powder mixture flows up into the blister hood 234, through the inlet 242 and into the bead chamber 250. The bead(s) 264 in the bead chamber move about at high speed within the chamber. This disburses powder and also helps to separate active drug particles from inert carrier particles, as described in International Patent Application PCT/US01/03248. The disbursed powder and air flows out through the engine tube 258 and is inhaled by the user.

Referring to FIG. 5, sheath air simultaneously flows out through an annular gap 259 between the engine tube 258 and the mouthpiece tube 144. The sheath air is drawn in from the sides of the mouthpiece 110 and contains no powder. Consequently, the powder laden air exiting the engine tube 258 is largely surrounded by sheath air. This helps to reduce settlement or deposition of drug particles on or in the mouthpiece 110 and potentially also reduces deposition on the user's lips, mouth or throat.

Figure 34A:
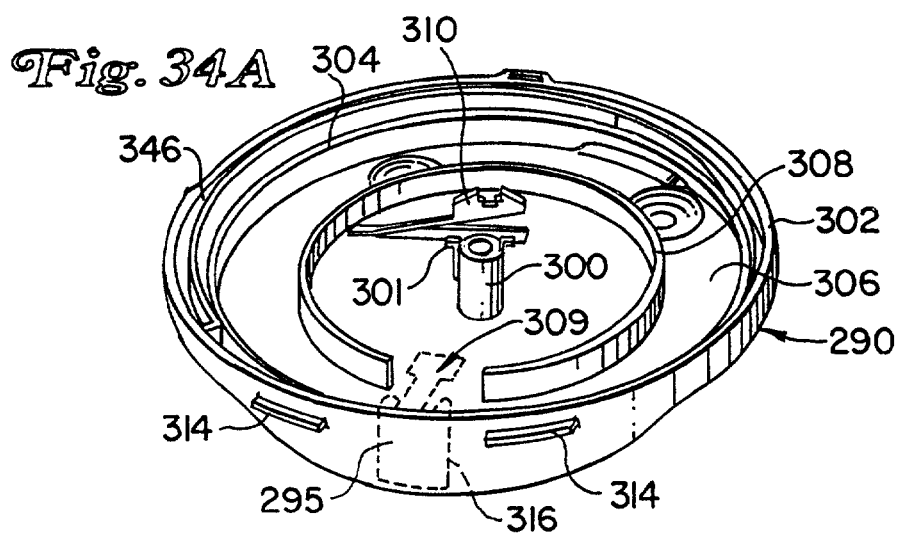
FIG. 34A is a top and front perspective view of the blister disk tray shown in FIGS. 2, 31, and 33.
Figure 35:
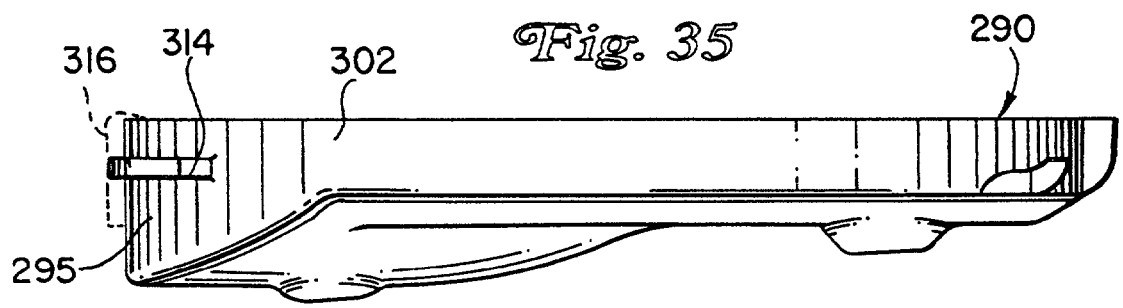
FIG. 35 is a right side view of the blister disk tray shown in FIG. 34.

After the user inhales the dose, the actuator 108 is returned to the home position AA as shown in FIG. 44. As this occurs, the ramp flange 212 pivots the dobber 162 back into its horizontal or home position. The arm 320 of the return spring 316 pushes the blister tab 352 back into a horizontal position. The tooth flange 211 on the advancing finger 208 of the actuator 108 moves down under the guide 174 (shown in FIG. 13) and through the actuator opening 182 in the base plate 102. The tooth flange 211 then pushes the ratchet lockout 310 down. The spoke 365 is then positioned between the angled sidewalls 370 of the y-slot 367 in the ratchet lock 310. The tooth 210 moves into a cutout 366 in the blister disk 106, and pivots the blister disk by one blister position. As the disk begins to move, the spoke 365 pushes the ratchet lock down further, by riding up and over the angled slot walls 370. The ratchet lock 310 then springs back up to engage around the next spoke. The inhaler 100 is then ready to deliver a subsequent dose. As shown in FIGS. 13 and 34A, the ratchet lock 310 extends up and in or across the tray 290 (as a horizontal chord), from the left or leading side of the tray. In these Figures, showing the inhaler and tray as viewed from above, the disk indexes clockwise. Consequently as the disk indexes, the position of the ratchet lock allows forward movement of the disk more easily than reverse movement. This reduces the force needed for normal forward indexing or rotation, and further guards against reverse indexing.

Referring to FIG. 13, the inhaler is preferably designed to provide fail-safe drug availability to the user. If the actuator is moved from the home or stored position AA in FIG. 44 to only an intermediate position, near or at position BB in FIG. 45, and is then returned to the home position AA before the blister is sheared open (i.e., with the seal layer still intact), no advancing occurs. In this case, the tooth 210 and the finger 208 of the actuator ride up and over the guide 174. The unopened and still sealed blister then remains in place in the blister opening position. This is achieved via the relative positions of the features on the actuator, the guide, and the dobber. On the other hand, if the actuator is moved far enough to begin shearing open a blister, so that the blister is no longer sealed, then the tooth 210 will have cleared the end of the guide 174, and it will move down under the guide and advance the blister disk to the next blister, as the actuator is returned to the home position. This largely prevents inhalation of a dose of powder which may have been exposed to the environment long enough to affect the power characteristics, by e.g., causing particle size growth, caking, clumping, etc.

With the inhaler as shown in FIG. 44, the dose windows 194 in the retainer 114, 180 in the base plate 102, and the first window 224 in the actuator 108 are aligned. Hence, the numbered blister aligned with the windows is visible. The user then can view how many doses remain on the blister disk. With the actuator in position CC as shown in FIG. 46, the numbered blister is again visible, with the second window 222 of the actuator aligned with the other windows. This provides visual confirmation to the user that the actuator forward movement is complete. When the actuator is in an intermediate position, as shown in FIG. 45, the arrows 226 are visible in the window 194. This provides a visual indication that the actuator should be further moved to the inhale position CC. The arrows partially blocks the dose number marked on the blister aligned in the windows.

The blister disk 105, in the embodiment shown, has space for up to 16 blisters. After all of the blisters have been opened and used, the blister disk tray assembly 104 is replaced. The tray retainer 106 is opened, as shown in FIG. 41. The tray assembly 104 is then pulled back out away from the inhaler 100, and a new tray assembly 104 is installed, as described above. As the actuator 108 must be at or near the home position AA to open or release the retainer 114, the dobber is automatically in its home or up position when the tray assembly 104 is changed. This prevents inadvertent opening of a blister when the new tray assembly is installed.

Referring to FIGS. 13 and 32, the blister hood 234 is vertically above the blister 356 in the blister opening position 309. Consequently, the powder in the blister 356 flows up, against the force of gravity, and is entrained in the air flow generated by the users inhalation. Test results show that about 10% of the powder remains in the up-facing blister. However, the fine particle fraction of the dose delivered remains high. This apparently occurs because the active drug particles which are more loosely attached to the carrier particles, flow out first from the upward facing blister 356. The residual powder remaining in the blister after the dose is delivered is of lower respirability because it includes larger particle sizes. Hence, fewer non-respirable particles move out of the blister 352 and into the dispersion engine 164, and fewer of them are inhaled by the user.

All surfaces in the inhaler that come into contact with the drug powder are part of a single subassembly, i.e., the dispersion engine including the hood and engine tube. This provides flexibility for use of the inhaler with different drugs.

The design shown in FIGS. 13 and 32 also acts as a multidose deterrent. When the blister 356 is sheared open, the powder 358 does not fall out of the blister. Rather, the powder remains in the blister until inhalation. Accordingly, if a blister is opened, but the user does not inhale and then subsequently moves the actuator again, the blister 356 is simply reclosed (the tab pivots closed, although the clear layer is severed), with the powder 358 remaining therein, and a new blister is brought into alignment to the blister opening position 309.

In a single use embodiment, the blister disk and/or tray or tray assembly may be part of or effectively permanently attached to the inhaler. The inhaler would then be discarded after all doses on the blister disk are used. In this embodiment, the retainer or latch 114 and tray features may be omitted.

Thus, novel dry powder inhalers and individual improved components or features have been shown and described. It will be apparent that various changes and substitutions may be made, without departing from the spirit and scope of the invention. The invention, therefore, should not be restricted, except by the following claims and their equivalents.

The invention claimed is:

1. An inhaler comprising:
   a housing;
   a mouthpiece on the housing;
   a powder dispersion engine in the housing including an engine tube extending into a mouthpiece;
   a hood adjacent to the powder dispersion engine; and
   a dobber at least partially over the hood.

2. An inhaler for delivering a dose of a dry powder pharmaceutical comprising:
   an inhaler housing;
   a blister opening position in the inhaler housing;
   a powder dispersion engine in the housing;
   one or more beads in the powder dispersion engine;
   a hood over the blister opening position and
   a powder pathway connecting from the hood into the powder dispersion engine.

3. An inhaler or delivering a dose of a dry powder pharmaceutical comprising:
   an inhaler housing;
   a blister opening position in the inhaler housing;
   a powder dispersion engine in the housing;
   a hood over the blister opening position; and
   a powder pathway connecting from the hood into the powder dispersion engine;
   an actuator adjacent the blister opening position for opening a blister; and
   a dobber at least partially over the hood, with movement of the actuator driving the dobber to shear open the blister, and with the dobber also pressing the blister hood down over the open blister.

4. An inhaler for delivering a dose of a dry powder pharmaceutical comprising:
   an inhaler housing;
   a blister opening position in the inhaler housing;
   a powder dispersion in the housing;
   a hood over the blister opening position with the hood having one or more grooves for adjusting bending characteristics of the hood; and
   a powder pathway connecting from the hood into the powder dispersion engine.

5. An inhaler for delivering a dose of a dry powder pharmaceutical comprising:
   an inhaler housing;
   a blister opening position in the inhaler housing;
   a powder dispersion engine in the housing;
   a hood flexibly attached to the inhaler housing over the blister opening position; and
   a powder pathway connecting from the hood into the powder dispersion engine.

6. The inhaler of claim 5 further including an actuator adjacent to the blister opening position for opening a blister.

7. The inhaler of claim 6 further comprising a dobber at least partially over the blister hood, with movement of the actuator driving the dobber to shear open a blister, and with the dobber also pressing the blister hood down over the open blister.

8. The inhaler of claim 5 with the hood displaceable from a first position to a second position, wherein the second position is closer to the blister opening position than the first position.

9. An inhaler for delivering a dose of a dry powder pharmaceutical comprising:
   an inhaler housing;
   a blister opening position in the inhaler housing;
   a powder dispersion engine in the housing;
   a chamber in the dispersion engine with one or more beads in the chamber;
   a hood over the blister opening position;
   a hood duct extending through the hood and connecting with the chamber, and forming a powder pathway connecting from the hood into the powder dispersion engine.

10. The inhaler of claim 9 with the powder dispersion engine including an engine tube extending into a mouthpiece attached to the inhaler housing.

11. The inhaler of claim 10 further including ribs extending radially inwardly into the engine tube.

12. The inhaler of claim 9 with the ribs forming an air flow restriction within the engine tube.

13. The inhaler of claim 9 further including an actuator adjacent to the blister opening position for opening a blister.

14. The inhaler of claim 13 further comprising a dobber at least partially over the blister hood, with movement of the actuator driving the dobber to shear open a blister, and with the dobber, also pressing the blister hood down over the open blister.

15. The inhaler of claim 9 further comprising a dust cap attached to the inhaler housing via a hinge oriented at an acute angle to the housing.

16. The inhaler of claim 9 further comprising a hood chamber in the hood, with the hood duct connecting into the hood chamber.

17. An inhaler for delivering a dose of a dry powder pharmaceutical comprising:
   an inhaler housing;
   a mouthpiece on the inhaler;
   a blister opening position in the inhaler housing;
   an actuator adjacent to the blister opening position;
   a powder dispersion engine in the housing;
   a hood over the blister opening position;
   an engine tube extending into the mouthpiece; and
   a dobber at least partially over the hood, with movement of the actuator driving the dobber to shear open a blister, and with the dobber also pressing the blister hood down over the open blister.

18. An inhaler for delivering a dose of a dry powder pharmaceutical comprising;
   an inhaler housing;
   a blister opening position in the inhaler housing;
   a powder dispersion engine in the housing;
   a hood over the blister opening position, with the hood displaceable from a first position to a second position, wherein the second position is closer to the blister opening position than the first position; and
   a powder pathway connecting from the hood into the powder dispersion engine.

19. The inhaler of claim 18 further comprising one or more beads in the powder dispersion engine.

20. The inhaler of claim 18 further comprising a blister at the blister opening position, with the blister having a shearable seal layer.

* * * * *